United States Patent [19]
Olins

[11] Patent Number: 5,232,840
[45] Date of Patent: Aug. 3, 1993

[54] ENHANCED PROTEIN PRODUCTION IN BACTERIA BY EMPLOYING A NOVEL RIBOSOME BINDING SITE

[75] Inventor: Peter O. Olins, Ballwin, Mo.

[73] Assignee: Monsanto Company, St. Louis, Mo.

[21] Appl. No.: 639,458

[22] Filed: Jan. 10, 1991

Related U.S. Application Data

[63] Continuation of Ser. No. 180,661, Mar. 30, 1988, abandoned, which is a continuation-in-part of Ser. No. 5,821, Feb. 4, 1987, abandoned, which is a continuation-in-part of Ser. No. 845,159, Mar. 27, 1986, abandoned.

[51] Int. Cl.$^5$ .................. C12P 21/00; C12N 15/18; C12N 15/67; C12N 1/21
[52] U.S. Cl. .................. 435/69.1; 435/69.4; 435/71.2; 435/172.3; 435/252.3; 435/252.33; 435/252.34
[58] Field of Search .................. 435/69.1, 69.4, 252.3, 435/252.34, 252.33, 172.1, 172.3, 71.2; 935/45

[56] References Cited

U.S. PATENT DOCUMENTS

| 952,496 | 8/1990 | Studier et al. | 435/194 |
|---|---|---|---|
| 4,508,827 | 4/1985 | Olsen | 435/91 |
| 4,772,555 | 9/1988 | Deboer | 435/172.3 |
| 4,935,370 | 6/1990 | Franke | 935/45 |

FOREIGN PATENT DOCUMENTS

| 178863 | 4/1986 | European Pat. Off. |
| 186069 | 7/1986 | European Pat. Off. |

OTHER PUBLICATIONS

Tabor et al. (1985), Proc. Natl. Acad. Sci., vol. 82, pp. 1074–1078.
Warburton et al. (1983), Nucleic Acid Res., vol. 11, pp. 5837–5834.
Stanssens et al. (1985), Gene, vol. 36, pp. 211–223.
Deboer et al. (1983), DNA, vol. 2, pp. 231–235.
Seeburg et al. (1983), DNA, vol. 2, pp. 37–45.
Bagdasarian et al. (1981), Gene, vol. 16, pp. 237–247.
Brosius, Jurgen et al. Complete nucleotide sequence of a 16S ribosomal RNA gene from *Escherichia coli*. Proc. Natl. Acad. Sci. USA 75:4801–4805 (1978).
Dunn, J. J. and Studier, W. F. Complete Nucleotide Sequence of Bacteriophage T7 DNA and the Locations of T7 Genetic Elements. J. Mol. Biol. 166:477–535 (1985).
Gold, Larry et al. *Escherichia coli* translational initiation factor IF3: A unique case of translational regulation. Proc. Natl. Acad. Sci. USA 81:7061–7065 (1984).
Gren, E. J. Recognition of messenger RNA during translational initiation in *Escherichia coli*. Biochimie 66:1–29 (1984).
Parker, Michael L. et al. Nucleotide Sequence of Bacteriophage T4 Gene 23 and the Amino Acid Sequence of its Product. J. Mol. Biol. 180:399–416 (1984).
Woese, Carl R. et al. Detailed Analysis of the Higher-Order Structure of 16S-Like Ribosomal ribonucleic Acids. Microbial Rev. 47:621–669 (1983).

Primary Examiner—Richard A. Schwartz
Assistant Examiner—Nancy Vogel
Attorney, Agent, or Firm—Dennis A. Bennett

[57] ABSTRACT

The present invention provides novel ribosome binding sites useful in enhancing protein production in bacteria. Methods, genes, vectors, bacteria and useful intermediates employing the novel ribosome binding sites of the present invention are also provided. A novel site of interaction different from a Shine-Dalgarno sequence between the 16S ribosomal RNA and messenger RNA is also provided.

8 Claims, 10 Drawing Sheets

FIG. 1

```
     BglII      ApaI                                                              XbaI
      —          —                                                                 —
5'-AGATCTGGGCCCTTCGAAATAATACGACTCACTATAGGGAGACCACAACGGTTTCCCTCTAGAAATAATTTTGTTTAACTTTAAGAAGGAGATATCCATGG-3'
 5 TCTAGACCCGGGAAGCTTATTATGCTGAGTGATATCCCTCTGGTGTTGCCAAAGGGAGATCTTTATTAAAACAAATTGAAATTCTTCCTCTATATAGGTACC
                                                                                              —
                                                                                           NcoI(NdeI)
```

FIG. 2

```
     BglII                                                        NcoI(NdeI)
      —                                                                —
5'-AGATCTGCTAGAATAATTTTGTTTAACTTTAAGAAGGAGATATATCCATGG-3'
10 TCTAGACGATCTTTATTAAAACAAATTGAAATTCTTCCTCTATATAGGTACC
```

FIG. 3

```
                         487
                          —
16S    3'-AUUGCAGUUACUCGUUUCCAUAAUUGAAAUGAGGGAAGGAG-5'
rRNA                          |||||||||
                              5'-UUAACUUUA-3'
15
16S rRNA
homology sequence
```

SEGMENT #1
5'-GATCTGGGCCCTTCGAAATTAATACGACTCACTATA-3'
    ||||||||||||||||||||||||||||||||||
  3'-ACCCGGGAAGCTTTAATTATGCTGAGTGATATCCCTCT-5'
        SEGMENT #2

SEGMENT #3
5'-GGGAGACCACAACGGTTTCCCTCTAGAAAT-3'
    ||||||||||||||||||||||||||||
  3'-GGTGTTGCCAAAGGGAGATCTTTATTAAAACAAAT-5'
        SEGMENT #4

SEGMENT #5
5'-TGTTTAACTTTAAGAAGGAGATATATC-3'
    |||||||||||||||||||||||||
  3'-TGAAATTCTTCCTCTATATAGGTAC-5'
        SEGMENT #6

ENHANCED PROTEIN PRODUCTION IN BACTERIA BY EMPLOYING A NOVEL RIBOSOME BINDING SITE

CROSS-REFERENCE TO RELATED APPLICATION

This is a continuation application of co-pending application Ser. No. 07/180,661 filed Mar. 30, 1988, now abandoned, which is a continuation-in-part of co-pending application Ser. No. 005,821, filed Feb. 4, 1987, now abandoned, which, in turn, is a continuation-in-part of co-pending application Ser. No. 845,159, filed Mar. 27, 1986, now abandoned.

TECHNICAL FIELD

The present invention is directed to nucleic acid sequences capable of enhancing gene expression in bacteria.

BACKGROUND OF THE INVENTION

The field of recombinant DNA technology has led to the development of numerous systems for producing a wide variety of naturally occurring and synthetic polypeptides in such microorganisms as yeast and bacteria. Notwithstanding these developments, there is a continuing need to provide for more efficient and economic methods for producing the polypeptides. In developing a process for commercial production of polypeptides, many factors are involved in optimizing the economic and efficient production of the polypeptides. Included among these factors are regulatory signals, which are nucleic acid (DNA and/or RNA) sequences involved with the regulation of gene replication, transcription and translation.

Translation is a multi-stage process which first involves the binding of messenger RNA (mRNA) to ribosomes. Beginning at the translation start codon, the mRNA codons are read sequentially as the ribosomes move along the mRNA molecule. The specified amino acids are then sequentially added to the growing polypeptide chain to yield the protein or polypeptide encoded in the mRNA.

As indicated, the first step in the translation process is the binding of the mRNA molecule to the ribosome. The nature of this interaction (i.e., binding) has been only partially elucidated. Analysis of RNase-resistant oligonucleotides isolated from bacterial translation initiation complexes indicate that a RNA fragment approximately 30 to 40 bases (nucleotides) in length comprises this initial ribosomes binding site. The start codon, which in most cases in an AUG, is located at or around the center of this ribosome binding site. Hence, a ribosome binding site (R.B.S.) is hereinafter understood to comprise a sequence of mRNA surrounding the translation start codon which is responsible for the binding of the ribosome and for initiation of translation.

In most procaryotic ribosome binding sites, the start codon is preceded by a purine rich region at a distance of 5 to 9 bases. The so-called Shine-Dalgarno sequence (Shine-Dalgarno, 1974) shows a variable region of complementarity with a region close to the 3' end of the 16S ribosomal RNA (rRNA). The importance of this region has been demonstrated both directly, by changing this sequence and also indirectly, by comparing the sequences of several known Shine-Dalgarno sequences. Both the Shine-Dalgarno sequence and 16S regions can be co-isolated from initiation complexes as an RNA duplex. The Shine-Dalgarno sequence has thus been found to base-pair with a specific sequence and within a specific region of the bacterial 16S ribosomal RNA. The Shine-Dalgarno region (SD-region) or SD-sequence is thought to assist the 30S particle in positioning itself at the proper place with respect to the start codon on the mRNA. Variation of the distance between the AUG and the SD-region and base composition in this spacer mRNA sequence have been found to affect the efficiency of the translation initiation process. Hence, attempts to optimize the translation efficiency of mRNA in such bacteria as $E.$ $coli$ have thus far centered around three components, the start/signal codon (AUG), the SD-region, and the length and nucleic acid composition of the spacer in between the AUG and SD-region. Other manipulations at the level of translation have included removal of mRNA secondary structure at or around the start of translation and/or substitution of preferred bacterial codons for otherwise less desirable codons in, for example, foreign mRNA. These latter manipulations must be made on an individual mRNA basis and thus do not provide a generic means by which polypeptide production, in general, may be enhanced.

Additionally, the state of the art has not reached a point where high-level expression of foreign gene products in such microorganisms as $E.$ $coli$ is a routine and predictable operation. The term "foreign" as used herein means genes, proteins and/or nucleic acid molecules not normally present within the specified host cell. Subtle features of the foreign gene, mRNA and protein can all affect the expression machinery of the microorganism leading to reduced accumulation of the desired product. Specifically, the efficiency of expression of known procaryotic genes varies by a factor of around 1,000 (Gold et al. 1984).

To achieve high levels of gene expression in such procaryotic hosts as $E.$ $coli$, it is necessary to use not only strong transcriptional promoters to generate large quantities of mRNA, but also to identify a ribosome binding site(s) that ensure that the mRNA is efficiently translated. There is, therefore, a need to create a binding site which correlates with a predictable increased or enhanced level of translation for a wide variety of genes (e.g. procaryotic and eucaryotic).

In one publication by Gold et al. (1984), a non-SD-region in an $E.$ $coli$ mRNA able to base-pair with the $E.$ $coli$ 16S ribosomal RNA was reported. However, said mRNA molecule was also found to contain a novel translation initiation codon, AUU, which codon is unique among $E.$ $coli$ mRNAs. (Gold et al. 1984).

SUMMARY OF THE INVENTION

The present invention provides an essentially pure nucleic acid molecule useful in enhancing the expression of a wide variety of genes, both procaryotic and eucaryotic, in bacteria. In one embodiment, the DNA sequence comprises the first about 100 nucleotides immediately 5' to the translation start codon of the bacteriophage T7 gene 10 coding sequence.

In another embodiment of the present invention, a nucleotide sequence comprising the sequence in FIG. 1 is provided.

In yet another embodiment of the present invention, a nucleotide sequence comprising the sequence shown in FIG. 2 is provided.

In another embodiment of the present invention, a nucleotide sequence is provided which sequence comprises from about five to about ten nucleotides able to base-pair with the bacterial 16S ribosomal RNA and which sequence is different from a SD-sequence.

In still another embodiment, a gene comprising a ribosome binding site which comprises a sequence complementary to a bacterial 16S ribosomal RNA domain different from a SD-sequence, is provided.

In a further embodiment, novel sequences in mRNA molecules comprising a sequence selected from the group consisting of 5'-UUAACUU-3', 5'-AACUUUA-3' and 5'-UUAACUUUA-3', which sequences are able to base-pair with the 16S ribosomal RNA of E. coli, are provided.

In still a further embodiment of the present invention, a novel site of interaction between the 16S ribosomal RNA and mRNA is described which interaction enhances the translation of mRNA and hence protein production in bacteria.

In a yet further embodiment of the invention, molecules which include the novel sequences of the present invention and a gene or genes associated with the production of a heterologous polypeptide product are provided which can be incorporated into the genome of a host bacterial cell. In preferred embodiments, such molecules provide for enhanced production in bacteria of such proteins as mammalian growth hormones, atriopeptigen and plant and bacterial enzymes.

In still a further embodiment of the present invention, methods are provided for achieving enhanced production of polypeptides comprising: causing expression of genomic DNA in bacteria, said DNA comprising a novel ribosome binding site of the present invention, a translation start codon, codons for a heterologous polypeptide and a translation stop codon, and thereafter recovering the heterologous polypeptide so produced.

Other embodiments include various genes, DNA vectors and transformed bacteria useful in the aforementioned methods and comprising said novel DNA sequences.

BRIEF DESCRIPTION OF THE FIGURES

In the following diagrammatic representations, the nucleic acid sequences are provided in a 5' to 3' orientation unless otherwise noted and wherein the nucleosides adenosine, guanine, cytosine, thymidine and uridine are denoted by A, G, C, T and U, respectively. The directional arrows represent the 5' and 3' orientation of the DNA coding sequences. "Ori" denotes the origin of replication for the plasmid vector DNA, "amp$^r$" denotes an ampicillin resistance gene, "Gm$^r$" denotes a gentamicin resistance gene, "LacZ" denotes the beta-galactosidase structural gene, "kb" denotes kilobases and "SD" denotes a consensus SD-sequence unless otherwise noted. Relevant restriction endonuclease sites are also shown. The DNA regions marked as described below are for diagrammatic purposes only and are not drawn to scale unless otherwise noted.

FIG. 1 depicts the DNA sequence of a synthetic double-stranded G10L sequence wherein the underlined nucleotide denote nucleotides which differ from the naturally occurring bacteriophage T7 gene 10 nucleotides, (***) denotes the nucleotides (i.e. bases) complementary to the E. coli 16S rRNA and (†††) denotes the SD-sequence. The (NdeI) denotes the location of the NdeI restriction endonuclease site in the naturally occurring bacteriophage T7 gene 10 coding sequence.

FIG. 2 depicts the DNA sequence of a 50 base-pair synthetic G10L molecule wherein the underlined nucleotides denote nucleotides which differ from the naturally occurring bacteriophage T7 gene 10 nucleotides, (***) denotes the nucleotides (i.e. bases) complementary to the E. coli 16S rRNA and (†††) denotes the SD-sequence. The (NdeI) denotes the location of the NdeI restriction endonuclease site in the naturally occurring bacteriophage T7 gene 10 coding sequence.

FIG. 3 depicts the RNA sequence of the E. coli 16S rRNA from nucleotide 447 to nucleotide 487. Also depicted is the 9 nucleotide sequence found in the G10L sequences of the present invention, which 9 nucleotide sequences can base-pair with the 16S rRNA as denoted by the vertical lines.

FIG. 13 depicts the construction of pMON5542 comprising a pEMBL plasmid having inserted therein Prec, a G10L sequence and a lacZ structural gene (LacZ).

FIG. 14 depicts the construction of two broad host range expression vehicles, pMON5757 and pMON5758, each comprising an IncQ replicon (IncQ), a gentamicin resistance selectable marker gene (Gm$^r$), Prec, a G10L sequence and a beta-galactosidase structural gene (LacZ).

FIG. 15 depicts the relevant contents of plasmids pMON5014, pMON5756, pMON5759, pMON5760 and pMON5761.

DETAILED DESCRIPTION OF THE INVENTION

Figure 4:
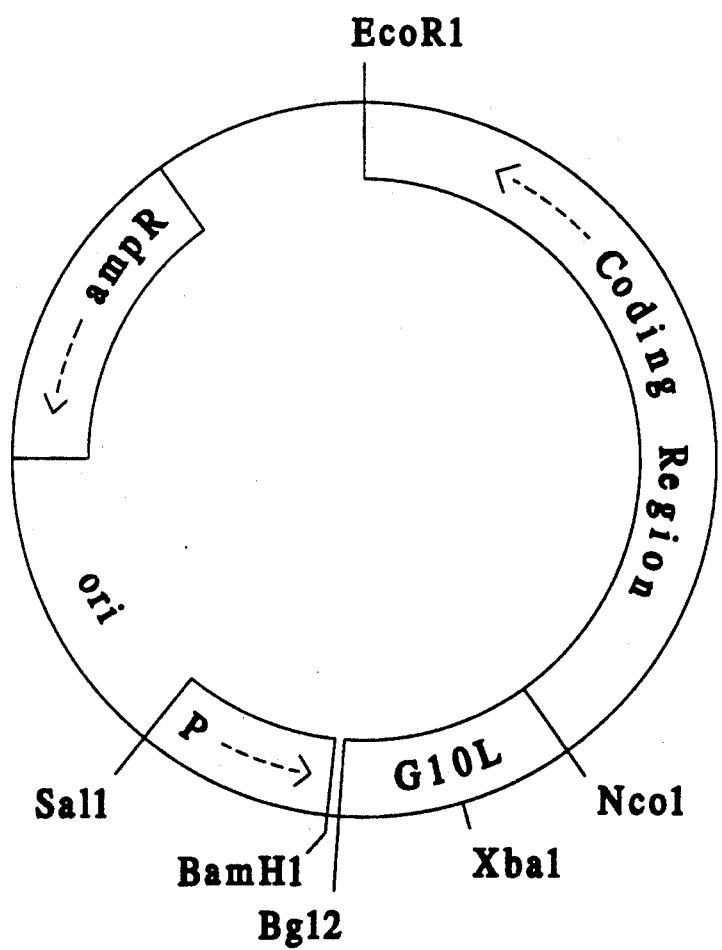
FIG. 4 depicts an expression vector comprising a G10L sequence, denoted "G10L." The "P" denotes a DNA sequence coding for a promoter able to cause transcription of DNA sequences in a host cell, "coding region" denotes the DNA sequence coding for a polypeptide and "amp$^R$" denotes an ampicillin resistance gene.

The present invention provides DNA sequences useful in enhancing protein production in bacteria such as E. coli. The discovery of such sequences and the use of expression vehicles comprising these sequences provides a valuable means for achieving increased production of expressible proteins, both endogenous and heterologous, in bacteria as well as achieving marked increased production of otherwise poorly expressed and/or accumulated proteins in bacterial host cells. Such proteins include, without limitation, such mammalian growth hormones as bovine growth hormone and porcine growth hormone, atriopeptigen, isopentyl transferase I, glutathione-S-transferase I, glutathione-S-transferase III, β-galactosidase, chloramphenicol acetyl transferase, and 3-enolpyruvyl shikimate 5-phosphate synthase, ferrite uptake regulation protein, insulin-like growth factor I and chimeric fusion protein.

In one embodiment of the present invention, the DNA sequences useful in enhancing polypeptide production in bacteria are found in the first about 100 nucleotides directly 5' (e.g. upstream) to the translation start codon of the bacteriophate T7 gene 10 coding sequence. The complete 100 nucleotide sequence comprises the promoter for the bacteriophage T7 gene 10 protein and the 5' non-translated region of gene 10 mRNA, said DNA or RNA equivalent sequence or fragments thereof are hereinafter collectively referred to as "G10L" sequences. Gene 10 codes for a coat protein, an abundant supply of which is required during bacteriophage T7 infection.

The entire DNA sequence of the bacteriophate T7 genome has been published by Dunn and Studier (1983) and is hereby incorporated by reference hereto. Thus, the herein identified G10L sequences can be obtained by isolation of the bacteriophate T7 DNA genome and separation of G10L sequences therefrom by techniques known to those skilled in the art or, alternatively, the G10L sequences of the present invention can be independently synthesized by conventional means. Once chemically synthesized or isolated, the G10L sequences of the present invention or equivalent nucleic acid sequences, as described more fully herein, represent essentially pure nucleic acid sequences or molecules. Thus, the term "essentially pure" when used to describe the nucleic acid (i.e. DNA or RNA) sequences or molecules of the present invention is understood to mean nucleic acid sequences or molecules essentially free from nucleic acid sequences with which they are associated in a nature. Examples of such essentially pure nucleic acid sequences or molecules include, but are not limited to, nucleic acid sequence enzymatically or chemically released from a larger (naturally occurring) molecule, chemically synthesized nucleic acid sequences free from naturally occurring intervening or contiguous sequences, and nucleic acid sequences in combination with sequences or molecules with which they are not naturally found associated or combined. Thus, due to the way by which essentially pure molecules are created, they are sometimes alternatively referred to as "synthetic" nucleic acid sequences or molecules.

In accordance with methods described herein and by employing conventional recombinant DNA techniques (Maniatis, et al. 1982), the synthetic G10L sequences can be inserted into the genomes of host cells. Furthermore, such insertion will result in enhanced protein production and/or accumulation relative to the G10L sequence employed and position within the gene at which the G10L sequence is inserted. The term "genome" as used herein means the total DNA (e.g. chromosomal and extrachromosomal) contained within a host cell. The term "gene" refers to DNA sequences which provide for production of protein(s) encoded therein. Typically, a gene comprises a promoter, a 5'-non-translated region, a translation start/signal codon, codons encoding protein(s), a translation stop/signal codon and 3'-non-translated DNA.

In a preferred embodiment, enhanced production of a desired product in such bacteria as $E.$ $coli$ was achieved by employing a gene comprising the approximately 100 nucleotide G10L fragment shown in FIG. 1.

Additionally, fragments of the 100 base-pair G10L sequence were shown to enhance protein production in such bacteria as $E.$ $coli$. Such fragments include a fifty nucleotide fragment having the DNA sequence shown in FIG. 2 and selected fragments comprising from about five (5) to about ten (10) nucleotides in length. Furthermore, it was discovered that selected fragments of the 100 base-pair G10L sequence could enhance product (e.g. protein) production when located a variety of positions within the ribosome binding site (R.B.S). Such locations include positions upstream (5') from the Shine-Dalgarno sequence, the spacer region between the SD-sequence and translation start/signal codon (AUG), and within the coding sequence (e.g. 3' or downstream from the AUG codon) for the desired product.

Thus, by following the teachings set forth herein, it is within the skill of those in the art to determine the precise nucleotide sequence(s) which optimally enhances protein production in such bacteria as $E.$ $coli$. For example, by creating nucleotide additions, substitutions, and/or deletions in the G10L sequences provided herein and/or by rearranging the location of said sequences within an expression vector and/or by positioning said sequences within the genome of such hosts cells as $E.$ $coli$, one can determine the precise nucleotide sequence(s) responsible for enhanced protein production in $E.$ $coli$ and/or other bacterial host cells.

Furthermore, analysis of desired protein producing systems in $E.$ $coli$ employing the G10L sequences of the present invention indicate that the enhanced protein production and accumulation observed was primarily achieved by an enhanced and/or more efficient translation of the mRNA molecules containing the G10L sequences and encoding the desired protein. While applicants do not wish to be bound by the following theory of mechanism, it is believed that the G10L sequences provide a novel ribosome binding site which binding site promotes as enhanced efficiency of translation of mRNA molecules containing said site. Indeed, when a comparative computer analysis of the G10L sequences with the 16S ribosomal RNA (rRNA) sequence published by Brosius et al. (1978) was performed, a region of the G10L sequences comprising about none nucleotides in length was discovered which is complementary (i.e. able to base-pair) to a novel region in the 16S rRNA of $E.$ $coli$ (see FIG. 3). Said complementary G10L sequence or region of homology comprises the nucleotides 5'-TTAACTTTA-3', denoted by an asterisk (*) in FIG. 1. This sequence corresponds to the mRNA sequence 5'-UUAACUUUA-3'. The foregoing G10L region of homology, functional fragments thereof and the corresponding RNA sequences therefore are hereinafter collectively referred to as G10L 16S rRNA homology sequences or regions. Functional fragments of the none nucleotide region of homology are understood to comprise those nucleotides which can base-pair with 16S rRNA and/or effect enhanced heterologous protein production in such bacteria as $E.$ $coli$. Examples of such functional fragments include molecules consisting of the sequence 5'-AACUUUA-3' and 5'-UUAACUU-3'.

The nucleotide length of the G10L 16S rRNA homology sequence of the present invention strongly suggests that the complementarity of this sequence to nucleotides 458 to 466 of the *E. coli* 16S rRNA is not a random event. Indeed, no other nine nucleotide sequence within the G10L was found which was able to base-pair with either the 23S rRNA or *E. coli* or anywhere else in the 16S rRNA. Furthermore, the G10L 16S rRNA homology sequence is only complementary to nucleotides 458 to 466 and to no other 9 nucleotide sequence in either the *E. coli* 16S rRNA or 23S rRNA. Thus, the site of interaction between the 16S rRNA and the G10L 16S rRNA homology sequence and fragments thereof represents a unique site of interaction.

Additionally, the precise complementarity and length of the G10L 16S rRNA homology sequence indicates that mRNA molecules containing this sequence can base-pair with a novel region of the 16S rRNA around position 460 forming a stable interaction between the 16S rRNA and the mRNA molecule. This interaction is believed to aid in the initiation of mRNA translation by directly stimulating translation initiation in a manner analogous to the SD-region and/or by allowing the mRNA to compete for binding to a limited pool of ribosomes thereby increasing the probability and/or frequency of translation mRNA molecules containing said sequence. Indeed, as described more fully in the examples hereinafter, insertion of the G10L 16S rRNA homology sequences within the R.B.S. of desired genes resulted in enhanced production of the protein encoded therein.

The need for a burst of coat protein expression in such bacteriophages may have led to the evolution of an mRNA sequence which exploits the ribosome in a manner different from normal translation. As demonstrated herein, this theory is supported by a finding of similar sequences in several bacteriophage coat protein mRNA's as compared to only a few of the *E. coli* mRNA's surveyed. Specifically, a comparison of the sequences published by Gren, E. J. (1984) and Parker et al. (1984) of mRNA molecules coding for proteins of highly expressed genes with the entire G10L sequence revealed the presence of G10L 16S rRNA homology equivalents in several mRNA molecules. Such mRNA molecules and their respective 16S rRNA complementary sequences include, but are not limited to, the following:

| mRNA | 16S rRNA Complementary Sequence |
| --- | --- |
| T7 gene 0.5A | ACUUUAC |
| T7 gene 0.5B | ACUUUACUU |
| T7 gene 2 | AACUUUG |
| T7 gene 3.8 | CUUUGUUC |
| T7 gene 9 | AACUUUA |
| T7 gene 17 | ACUUUA |
| lambda E gene | UUUUAC or GGCUUU |
| Q-beta gene C | AACUUUG |
| phi-X174 gene F | ACUUU |
| G4 gene J | ACUUU |
| *E. coli* pyr B | UUUUAC |
| *E. coli* enc C | AACUUUA |
| clodfl3imm | CUUUA |
| T4 gene 23 | AACUUU |
| MS2/R17 gene C | UAACUUUACU |
| *E. coli* tnaA | AACUUUA |
| T7 gene 11 | GACUUUA |

| mRNA | 16S rRNA Complementary Sequence |
| --- | --- |
| *E. coli* elt A | UAACUUU |

A 16S rRNA homology sequence embracing the G10L 16S rRNA homology sequences and equivalent sequences found in the aforementioned mRNA molecules comprises the formula: $5'-Z_m XUU(B)_n-3'$ in which X is C or U, m and n are 0 or 1 with the proviso that at least one m or n is 1, Z is selected from the group consisting of A, G, AA, GG, GA, UA, UAA and UUAA and B is selected from the group consisting of U, UA, UG, UAC, UACU, UACUU and UGUUC. In preferred 16S rRNA homology sequences X is C, m and n are both 1, Z is selected from the group consisting of A, AA, UA, UAA and UUAA and B is selected from the group consisting of UA, UAC and UACU. In another preferred 16S rRNA homology sequence X is C, m is 1 and n is 0 and Z is UUAA.

Accordingly, other sequences which will enhance protein production in bacteria and are considered to be equivalent to the G10L sequences and/or G10L 16S rRNA homology sequence of the present invention can be constructed by conventional techniques. For example, equivalent sequences comprising the 16S rRNA complementary sequences or fragments thereof present in the enumerated mRNA molecules can be chemically synthesized. Similarly, nucleotide additions, substitutions, deletions and/or inversions in the G10L sequences can be made by conventional chemical, enzymatic and recombinant DNA techniques so that essentially equivalent enhancement in protein production is achieved with modified G10L sequences.

Surprisingly, the region of 16S rRNA homology in these mRNA molecules was found to be located either 5' (upstream) from the SD-region or 3' (downstream) to the translation start codon. These findings suggest that the exact location in the mRNA molecule of this novel 16S rRNA homology sequence may not be critical. Indeed, as shown in the examples below, the G10L 16S rRNA homology sequence and/or fragments thereof can be located upstream (5') from the SD-region, in the spacer region between the SD-sequence and the translation start (AUG) codon, and/or 3' (downstream) to the translation start codon. Additionally, more than one 16S rRNA homology sequence and/or equivalents thereof can be present in a single mRNA molecule. In a preferred embodiment of the present invention, at least one G10L 16S rRNA homology sequence is located 5' (upstream) to the translation start codon as its location 3' to the start codon would require that codons in the 16S rRNA homology sequence specify amino acids contained within the protein to be produced.

In another embodiment, identification of a G10L 16S mRNA homology region within the G10L sequences of the present invention revealed a novel site (e.g. sequence or region) of interaction with mRNA molecules on the 16S rRNA.

The entire nucleotide sequence of *E. coli* 16S rRNA has been published by Brosius et al. (1978) and said sequence is hereby incorporated by reference hereto. The novel region of interaction in the 16S rRNA comprises an approximate 40 nucleotide fragment comprising from about nucleotide 447 to about nucleotide 487, as shown in FIG. 3, with a preferred region of interaction from about nucleotide 458 to about nucleotide 466.

This novel region of interaction in the 16S rRNA is about 1000 bases removed from the 16S rRNA sequence that interacts with the SD-region. Having now discovered a novel region of interaction between the 16S rRNA and mRNA molecules, it is possible to design a mRNA sequence capable of binding (i.e. base-pairing) to the 16S rRNA within said novel 16S rRNA nucleotide region. Said sequence, which falls within the class of 16S rRNA homology sequences previously described would comprise a non-SD-region of at least a sufficient number of nucleotides able to achieve a stable interaction between two distinct nucleic acid molecules. A preferred sequence would contain at least 5 nucleotides and possibly not more than 10.

Based upon the nucleotide sequence, shown in FIG. 3, from about nucleotide 447 to about nucleotide 487 in the 16S rRNA, one of skill in the art can construct "degenerate" mRNA sequence which can base-pair with this domain of the 16S rRNA. The term "degenerate" refers to the fact that the purine adenosine (A) preferentially base-pairs with pyrimidines thymidine (T) in DNA and uridine (U) in RNA. Analogously, while the purine guanidine (G) preferentially base-pairs with pyrimidine cytidine (C), stable but less favorable base-pairing can occur between G and the pyrimidine U. DNA sequences (e.g. genes) and mRNA sequences which comprise such a degenerate sequence or fragments thereof are considered to constitute equivalents of the preferred G10L sequences. The preferred length of such a degenerate sequence of sequences complementary to this domain of the 16S rRNA is from about 5 to about 10 nucleotides with a most preferred length being about 7 to 9 nucleotides.

Thus, it is understood that equivalent nucleic acid sequences capable of enhancing protein production in bacteria other than *E. coli* can now be determined. Specifically, by employing the above described methods, these equivalent sequences can be determined by analysis of mRNA sequences of highly expressed proteins of bacteriophage able to infect such other bacteria and/or by analysis of mRNA sequences of highly expressed proteins in these bacteria and/or by constructing a sequence(s) complementary to such other bacterial 16S rRNA region(s) able to base-pair with those bacteriophage mRNAs. Alternatively, the sequence of the 16S rRNAs of bacteria other than *E. coli* can be determined by conventional means and a sequence comprising a sufficient number of nucleotides able to achieve a stable interaction (i.e. base-pair) between two distinct nucleic acid molecules can be created. Specifically, Woese et al. (1983) have derived a model for the secondary structure of *E. coli* 16S rRNA. The overall architecture of this secondary structure has been conserved among a wide variety of 16S-like RNAs from diverse organisms (Gutell et al., 1985). The rules of this architecture permit the approximate secondary structures to be predicted for the 16S-like RNAs from other organisms, once the primary sequence has been determined. One structural domain of the *E. coli* 16S rRNA consists of a region from around nucleotide number 447 to 487 (Woese et al., 1983) identified in the present invention. Thus, mRNA sequences can be devised which can form a stable base-paired interaction with a portion of the equivalent structural domain of the 16S-like RNA in another organism, hence enhancing gene expression in that organism. Sequences can be engineered into the mRNA of such an organism which would enhance the translation of the engineered mRNA in that organism.

Examples of such organisms include, but are not limited to, Proteus species (e.g. vulgaris), Serratia species (e.g. marcescens), Bacillus species (e.g. *subtilis, brevis, stearothermophilus, thuringiensis*), Pseudomonas species (e.g. *aeruginosa, testosteroni*), Mycoplasma species (e.g. *capricolum*), Anacystis species (e.g. *nidulans*) or Streptomyces species. Such complementary sequences would have a length of from about 5 to about 10 nucleotides with preferred length being about 7 or 9 nucleotides.

In one embodiment of the present invention, essentially pure or synthetic G10L sequences were operatively joined to DNA molecules (e.g. expression vehicles or chromosomal DNA) which included at least one heterologous gene which was associated with the production of a product (i.e. peptide or protein). The term "heterologous" as used herein means genes, DNA sequences and/or products not naturally associated with or coded for by the bacteriophage T7 genome. The term "product(s)" includes both proteins directly encoded by an expressed gene and proteins produced as a result of some action on or by the protein encoded in the gene. The operative joining of these essentially pure sequences to a DNA molecule can be achieved biologically and/or by enzymatic and/or chemical means including, for example, by means of a ligase. In the resulting synthetic DNA molecule or gene, the G10L sequence and DNA coding sequences and/or gene components associated with production of desired peptides or proteins can be contiguous or noncontiguous, limited only by the ability of the G10L sequence to effect enhanced translation and, thus, expression of the gene or genes.

In one embodiment, the 100 base-pair G10L sequence was inserted into a gene between the DNA sequence encoding a transcriptional promoter and was contiguous with the translation start codon of the DNA sequence encoding the desired product as shown in FIG. 4. In another embodiment, a G10L sequence comprising a 16S rRNA homology region was inserted into a gene so that the 5' end of the G10L 16S rRNA homology sequence was contiguous with the 3' end of the SD-sequence and the 3' end of the 16S rRNA homology sequence was contiguous with the translation start (AUG) codon.

In constructing a gene or genes which contain a G10L sequence, it is anticipated that any promoter capable of causing transcription in bacteria of such a gene or genes can be employed. Examples of such promoters are well known and available to those skilled in the art and include, without limitation, such bacterial, viral and plasmid gene promoters as the $\beta$-galactosidase, recA, tryptophan, tac, tetracycline resistance and lambda $P_L$ promoters (Rosenberg and Court, 1979). The preferred promoters include the recA, lambda $P_L$ and tryptophan promoters. The DNA sequences of these promoters have been published and DNA molecules containing these promoter sequences can be isolated either by cloning the desired regions, or more conveniently, by chemically synthesizing them. Direct synthesis has the advantage that suitable restriction sites, exemplified by the SalI and BamHI restriction sites shown in FIG. 4, can be incorporated at the ends of the DNAs.

Similarly, any heterologous gene or DNA sequence which is associated with production of a product in bacterial host cells can be employed. Such genes or DNA sequences can be chemically synthesized, isolated from appropriate gene or cDNA libraries and/or enzymatically constructed by conventional methods. The heterologous products encoded in such genes or affect by protein(s) encoded in such genes are typically useful peptides or polypeptides. Such products can include peptides or proteins of both procaryotic and eucaryotic origin. As detained in the examples below, heterologous products which can be produced in such bacteria as *E. coli* in enhanced amounts using the invention are, without limitation, animal growth, insulin-like growth factor, transforming growth factor-alpha, tissue plasminogen activator, viral antigens, interleukins, fusion proteins and useful procaryotic and eucaryotic enzymes. It is understood that these and other heterologous proteins produced in bacteria in accordance with the methods of the present invention can be recovered from the bacteria and/or reconstituted to their respective native conformation by means known to those of skill in the art.

In another important embodiment, the G10L sequences of the present invention were operatively joined to genes containing transcription termination sequences. The operative joining of said sequence led to the discovery that protein production and/or accumulation in bacteria can be further enhanced by the presence of both a G10L and transcription termination sequence in a given gene. Specifically, it was discovered that whereas the operative joining of a G10L sequence to a gene yielded as much as a 300 fold increase in protein production as compared to otherwise identical genes lacking a G10L sequence, the addition or operative joining of a transcription termination sequence to G10L sequence-containing genes yielded a further two to four fold increase in protein production.

Transcription termination sequences useful in the present invention include, without limitation, those found in bacteriophage and bacterial DNA (see Holmes et al., 1983). Preferred transcription termination sequences include a T4 gene 23 terminator (Parker et al., 1984), a P22 gene ant terminator (Berget et al., 1983), a ColE1 terminator (Olins et al., 1981) and the synthetic terminator sequence described more fully in the examples below which are derived from a bacteriophate T7 10 gene terminator (Dunn and Studier, 1983).

Factors found to affect enhancement of desired protein production in bacteria when transcription terminators are employed include the orientation of the transcription terminators in the gene, number of terminator sequences used and number of nucleotides interspacing the 3'-end of the coding sequence and 5'-end of the transcription termination sequence. Although these factors can vary depending upon the DNA coding sequence employed, a preferred orientation is one in which the first terminator downstream of the DNA coding sequence is in the same orientation as that of the DNA coding sequence. A preferred number of terminators is two.

In one embodiment of the present invention a DNA segment corresponding to the first 100 base pairs (bp) immediately upstream of the coding sequence for the bacteriophage T7 gene 10 was constructed by chemical synthesis based upon the published sequence, Dunn and Studier (1983), of the bacteriophage T7 genome. Specifically, said G10L sequence, shown in FIG. 1, was constructed to correspond to the naturally-occurring G10L sequence with the following modifications. BglII and ApaI restriction endonuclease sites were inserted at the 5'-end of the G10L sequence and a NcoI restriction endonuclease site was inserted at the 3'-end of the G10L sequence. The insertion of these restriction endonuclease sites resulted in the nucleotide substitutions denoted by an underline in FIG. 1. The insertions of these two restriction sites at the ends of the G10L sequence was made to facilitate subsequent insertion of the G10L fragment into existing expression vectors or vehicles. Thus, while the BglII and NcoI restriction sites represent the preferred restriction endonuclease sites for purposes of insertion of the G10L sequences into the preferred expression vectors of the present invention, other conventional restriction endonuclease sites may be alternatively employed. For example, a 50 bas-pair G10L sequence able to enhance protein production of *E. coli* can be obtained from the bacteriophage T7 genome by cleavage with NdeI and XbaI (see FIG. 1) without resulting in any nucleotide substitutions in the native nucleotide sequence. The 50 base-pair G10L sequence so obtained can subsequently be inserted into genomic DNA by conventional means. Additionally, other methods known to those skilled in the art for insertion into or joining of nucleic acid molecules with, for example, any available cloning or expression vehicle or chromosomal DNA can be alternatively employed. Such other methods include, without limitation, blunt-end ligation or chemical synthesis of nucleic acid fragments comprising the G10L sequence of the present invention with a heterologous gene (Maniatis et al., 1982).

In one embodiment, a DNA molecule containing the G10L sequence shown in FIGS 1 or 2 was inserted into an expression vector comprising a promoter and DNA sequence encoding a heterologous protein. An expression vector or vehicle is herein understood to comprise a DNA molecule such as a phage, plasmid or cosmid DNA capable of transforming a bacterial host cell, such as *E. coli*, and capable of causing expression of a desired gene in said host cell. Any expression vector such as phage, plasmid or cosmid vectors known and/or available to those skilled in the art can be employed. The preferred vectors include such pBR plasmid vectors as pBR327. Soberon et al. (1980). FIG. 4 illustrates a generic example of such a preferred plasmid expression vector comprising a G10L sequence of the present invention. Such a plasmid expression vector contains an origin of replication (ori), in the instant example derived from pBR327, a drug resistance marker (amp$^r$) allowing selection of bacterial cells carrying the plasmid and various unique restriction endonuclease sites, allowing insertion, into the plasmid, of a promoter (P), ribosome binding site (i.e. a G10L sequence) and a DNA coding region for the protein or peptide of interest.

In a preferred expression vector shown in FIG. 4, the plasmid from the SalI restriction site to EcoRI site (in a clockwise direction) is derived from pBR327 and carries an ori and the betalactamase gene (amp$^r$). The amp$^r$ gene allows for selection by growth of transformed host cells in ampicillin containing medium. The SalI restriction site to BamHI (in a counter-clockwise direction) contains a segment of DNA which acts as a promoter for transcription in bacteria. The unique BglII site to the NcoI site (in a counter-clockwise direction) contains a ribosome binding site (i.e. a G10L sequence); and the DNA sequence coding for a heterologous polypeptide begins at the unique NcoI site and terminates upstream of the EcoRI site (in a counter-clockwise direction). The NcoI restriction site typically overlaps the translation initiation codon (e.g. ATG) for the gene.

Once such a vector is constructed, the essential components can be readily exchanged for alternative components by conventional means. For example, by using the indicated restriction endonuclease sites flanking the promoter, R.B.S. (e.g. G10L sequence of SD-region) and coding sequence, additional and/or alternative DNA sequences can be inserted by enzymatic or chemical linkage. Indeed, other antibiotic resistance genes can be substituted as a transformation marker in place of the ampicillin resistance gene (denoted amp' in FIG. 4), a promoter or promoters previously described and/or available to those skilled in the art can be inserted as well as any DNA coding sequence previously isolated or chemically synthesized. The DNA coding sequence so inserted can encode a single heterologous polypeptide or fragment thereof, a polyprotein or a fusion protein.

Alternatively, as previously indicated, enhanced protein production in bacteria can be achieved by inserting a G10L sequence into the bacterial chromosome, by conventional means, alone or in combination with a heterologous gene to achieve enhanced production of a heterologous polypeptide.

In one embodiment, the expression vector containing a G10L sequence was employed to transform bacterial host cell such as E. coli. the terms "transform" and "transformation" are herein understood to comprise any method for introducing exogenous DNA into the genome of a host cell. Such methods include, without limitation, transformation, transduction, transfection, conjugation and integration into chromosomal DNA.

The transformed host cell was selected (Maniatis et al. 1982) and cultured under conditions which cause the expression of the heterologous protein. The heterologous protein so produced can then be purified by techniques known to those skilled in the art and/or assayed for production by means consistent with the protein produced (e.g. Western blot, radioimmunoassay, protein staining of a protein gel and/or enzymatic activity). Such purification and/or protein assay methodologies can also be employed to ascertain the level(s) or protein production.

In one embodiment, the determination of enhanced protein production and/or accumulation achieved by employing the G10L sequences of the present invention was made by comparison to the amount of protein produced employing otherwise equivalent expression systems in which the G10L sequences were absent. Specifically, plasmid expression vectors were constructed which either contained a G10L sequence or contained a control SD-region. The control SD-region employed comprises the sequence:

```
    BglII           ↑↑↑↑↑↑↑           NcoI
5'-AGATCTGTTGTAAGGAGTCTAGACCATGG-3'
   TCTAGACAACATTCCTCAGATCTGGTACC
``` wherein the (↑↑↑) denotes the SD-sequence and wherein the entire above sequence represents a synthetic sequence derived from several previously published SD-sequences (Scherer et al. 1980). As shown in the examples below, significant enhancement of protein production for a wide variety of proteins (e.g. mammalian, plant and bacterial) was achieved when the G10L sequences of the present invention were employed as compared to otherwise equivalent expression systems containing the control SD-sequence (i.e. not containing a G10L sequence). The term significant enhancement refers to at least a 1.6 fold increase in protein accumulation. Indeed, greater than 300 fold increases in protein accumulation were observed for such proteins as growth hormone and isopentyl transferase I when a G10L sequence was employed as compared to expression systems lacking a G10L sequence. A preferred G10L sequence is the sequence shown in FIG. 1. Additionally, as shown more fully in the examples below, this significant enhancement was achieved irrespective of the promoter employed. Thus, the G10L sequences of the present invention can be employed in any selected expression system to achieve enhanced protein production in bacteria for both procaryotic and eucaryotic heterologous polypeptides. The preferred bacteria being an E. coli.

Microorganisms and Plasmids

The following microorganisms have been deposited with the American Type Culture Collection (ATCC), 12301 Parklawn Drive, Rockville, Md., 20852, U.S.A.:

ATCC 39936—E. coli W3110
ATCC 53469—E. coli N6405
ATCC 67043—E. coli M5219 (pMON5510)
ATCC 67044—E. coli JM101 (pMON6002)
ATCC 53023—E. coli W3110 (pMON3213)

These deposits are available to the public upon the grant of a U.S. patent and will be available for the life of any such U.S. patent having the benefit of the filing date of this application. However, it should be understood that the availability of a deposit does not constitute a license to practice the subject invention in derogation of patent rights granted by governmental action. Furthermore, the present invention is not to be limited in scope by the microorganisms deposited since the deposited embodiments are intended only as specific illustrations of the invention.

EXAMPLES

Materials and Methods

All oligonucleotides were synthesized employing an Applied Biosystems DNA synthesizer in accordance with the procedure set forth by the manufacturer, Applied Biosystems, Inc., Foster City, Calif. Unless otherwise noted all specialty chemicals were obtained from Sigma (St. Louis, Mo.). Restriction enzymes and DNA modifying enzymes were purchased from New England Biolabs (Beverly, Mass.), New England Nuclear (Boston, Mass.) and Bethesda Research Laboratories (BRL) (Gaithersburg, Md.) and used in accordance with manufacturer's directions. T4 DNA ligase was purchased from Promega Biotec (Madison, Wis.) and used in accordance with manufacturer's specifications. $^{32}$P-labeled nucleotides were purchased from Amersham (Arlington Heights, Ill.). E. coli JM101 was obtained from Dr. J. Messing, University of Minnesota (St. Paul, Minn.) and may be obtained from the ATCC under accession No. 33876. E. coli W3110 can be obtained form the ATCC (Rockville, Md.) under ATCC accession number 39936. E. coli N6405 were obtained from Dr. M. Gottesman, National Institutes of Health (Bethesda, Md.) and can be obtained from the ATCC under ATCC accession number 53469. E. coli strain BW313 can be obtained form Dr. Thomas Kunkel, Laboratory of Genetics, National Institute of Environmental Health Sciences, Research Triangle Park, N.C., 27709. Vectors pBR327 and M13mp9 can be obtained from Pharmacia (Piscataway, N.J.). Plasmid pUC18 described by Yanisch-Perron et al., 1985) may also be obtained from Pharmacia (Piscataway, N.J.). Vector M13mp19 was obtained from New England Biolabs (Beverly, Mass.).

All product (i.e. peptide or protein)-specific antibodies were obtained as follows. Protein-specific antibody production was based on the method of Vatukaitis (1981). For bovine growth hormone (BGH), a female New Zealand White rabbit was immunized with intramuscular injections of 1000 μg recombinant bovine growth hormone (rBGH) in Freund's Complete Adjuvant. The rabbit received booster injections consisting of 1000 μg rBGH in Freund's Incomplete Adjuvant (FIA) at four and eight weeks and an additional booster injection of 500 μg rBGH in FIA at sixteen weeks. For the detection of atriopeptigen and antiserum was raised against a peptide, atrial peptide II (AP2), corresponding to the C-terminus of the atriopeptigen molecule. A female New Zealand White rabbit was immunized with multiple intradermal injections of a solution containing 100 μg of rat AP2 and 150 μg of Keyhole Limpet Hemocyanin (KLH) (Sigma, St. Louis) in Freund's Complete Adjuvant. The rabbit received a booster injection consisting of 100 μg of rat AP2 and 150 μg of KLH in Freund's Incomplete Adjuvant at eight weeks. The rabbit had serum antibody titer in an ELISA against KLH.

The growth media for $E.$ $coli$ and conditions for selection of cells carrying plasmids containing an ampicillin resistance ($amp^r$) marker employed were as described in Maniatis et al. (1982). All bacterial growth media components and antibiotics were obtained from either Sigma (St. Louis, Mo.) or Difco Laboratories (Detroit, Mich.). Specifically, cells were grown in the presence of 200 μg/ml ampicillin to select for the presence of plasmid DNA. The growth medium used was either 2×YT medium or M9 minimal medium, Maniatis et al. (1982), supplemented with 0.2% (w/v) glucose, 0.5% (w/v) Casamino acids obtained from Difco Laboratories (Detroit, Mich.) and 5 μg/ml thiamine. Transformation of $E.$ $coli$ host cells with recombinant DNA cloning and expression vectors was performed as described in Maniatis et al. (1982).

Induction of transcription from the recA promoter was conducted briefly as follows. $E.$ $coli$ JM101 or W3110 host cells carrying expression plasmids were grown in supplemented M9 minimal medium, described above, to a cell density of 150 Klett units (measured with a Klett-Summerson meter, Klett Mfg. Co., New York, N.Y.), followed by the addition of one twentieth volume of nalidixic acid solution (10 mg/ml, dissolved in 0.1M NaOH). Growth was continued for several hours after induction, with aliquots taken at one hour intervals to determine the peak of heterologous protein production. A high level of aeration was maintained throughout the growth in order to achieve maximal production of the desired gene product, and the temperature of the culture was maintained at 37° C.

Induction of transcription from the tryptophane (trp) promoter was conducted briefly as follows. $E.$ $coli$ JM101 or W3110 host cells carrying expression plasmids were grown overnight in LB medium (Maniatis et al. 1982) containing 100 μg/ml ampicillin, at 37° C. Cultures were then diluted 50-fold into supplemented M9 medium, described above, containing 5 μg/ml tryptophan. Growth was continued for several hours, with aliquots taken at one hour intervals to determine the peak of heterologous protein production.

Induction of transcription from the lambda $P_L$ promoter was conducted briefly as follows. $E.$ $coli$ N6405 host cells carrying expression plasmids were grown as described above, except that cultures were grown at 30° C. until they reached a cell density of 150 klett units. The cultures were thereafter grown at 42° C. which inactivated the temperature-sensitive lambda repressor contained in the chromosomes of the host cells. Inactivation of the repressor permitted transcription from the $P_L$ promoter to take place. Aliquots were taken at one hour intervals after induction to determine the peak of heterologous protein production.

The levels of heterologous protein produced in the host cells were determined by such protein-specific assays as enzyme activity, Western immuno-blotting (Renart et al. 1979) or protein staining of an SDS-polyacrylamide gel (Laemmli, 1970). For example, the levels of beta-galactosidase (lacZ) produced were determined as follows. Cells containing the expression plasmid were grown in LB medium (Maniatis et al. 1982) containing 200 ug/ml ampicillin until they reached an optical density of about 1.0 at 600 nm wavelength. Cells from 1.0 ml of culture were harvested by centrifugation, and the pellet was resuspended in 1.0 ml 10 mM Tris, pH 7.5. Cells were broken open by sonication and any insoluble residue was removed by centrifugation. The extract was diluted 2 to 100 fold with Z Buffer (comprising, per 100 mls, 1.61 g $Na_2HPO_4.7H_2O$, 0.55 g $NaH_2PO_4.7H_2$), 75.0 mg KCl, 25.0 mg $MgSO_4.7H_2O$, and 0.270 ml beta-mercaptoethanol and adjusted to pH 7.0), prior to assay in order to get a measurable activity. 25–100 μls of diluted samples was added to Z Buffer to a final volume of 1.0 ml. The tubes were equilibrated at 28° C. and 0.2 mls of O-nitrophenyl-β-galactopyranoside (4 mg/ml in 0.1M phosphate buffer, pH 7.0) was added. The reaction was allowed to proceed until a noticeable yellow color developed. The reaction was then stopped by adding 0.5 ml 1M $Na_2CO_3$, and the absorbance was measured at 420 nm. The units of Lac Z equaled 1000 multiplied by the optical density at 420 nm divided by the reaction time, in minutes, multiplied by the volume of sample used, in milliliters (ml), multiplied by the optical density (OD) of the original culture at 600 nm.

The levels of glutathione-S-transferase I (GSTI) were determined in accordance with the procedure described by Habig and Jakoby (1981), briefly as follows. $E.$ $coli$ JM101 cells containing expression plasmids comprising the GSTI gene were grown in supplemented M9 medium, previously described, to a density of Klett 150 and the promoter induced, as previously described. After induction, the cells were cultured for 3 hours at room temperature and then a 1 ml aliquot was taken. The cells in the aliquot were recovered by centrifugation and the pellet was resuspended in 1 ml water. A cell lysate was prepared by vortexing with glass beads. The glass beads and cell debris were then removed by centrifugation and the supernatant was then assayed for GST I activity as follows. 1 ml of reagent A comprising 100 mM $KHPO_4$, pH 6.5, and 10 mM glutathione, and 33 μl of reagent B comprising 100 mM chlorodinitrobenzine in ethanol, were mixed with 10 to 100 μl of cell supernatant. The rate of change in absorbance at 340 nm wave length was then monitored as described by Habig and Jakoby (1981). All activities were corrected for the initial density of the cell culture.

The levels of chloramphenicol acetyl transferase (CAT) were determined by assaying for enzyme activity as follows. $E.$ $coli$ JM101 cells containing the plasmid are grown in supplemented M9 medium to a density of approximately 300 Klett units. Cells from 1.0 ml of culture were harvested by centrifugation and the pellet was resuspended in 1.0 ml Tris-HCl, pH 7.8, and broken open by sonication. Cell debris was removed by centrifugation and the supernatant was used for assay. The lysate was diluted with Tris-HCl, pH 7.8, to a concentration determined by the activity in the sample. 50 μls of diluted lysate was added to 1.0 ml assay buffer comprising 100 mM Tris-HCl, 0.1 mM acetyl CoA, 0.4 mg/ml 5,5'-dithiobis-2-nitrobenzoic acid and chloramphenicol was added to a final concentration of 0.1 mM to start the reaction. The amount of CAT activity was determined by reading the change in adsorption at 412 nm at 37° C. The net change in extinction per minute is divided by 13.6 to give units of enzyme (CAT) in the curette. All activities were corrected for the initial density of the cell culture.

The levels of atriopeptigen, bovine growth hormone and porcine growth hormone (PGH) were determined by Western immunoblotting in accordance with the method described by Renart et al. (1979) or by protein staining (e.g. with Coomassie Brilliant Blue) of an SDS-polyacrylamide gel (Laemmli, 1970).

The levels of 3-enolpyruvyl shikimate 5-phosphate synthase (EPSP) were determined as follows. Cells carrying an EPSP expression vector were grown to mid-log growth phase and 1 ml aliquots were harvested by centrifugation. The pellets were washed in 10 mM Tris pH 8, 1 mM Na₂EDTA, 0.1M NaCl, and re-suspended in 2 ml 50 mM sodium acetate buffer, pH 5.2. All operations were performed at 0° C. The pellets were lysed by sonication, and cell debris was removed by centrifugation. Two μl aliquots of the extract were assayed for EPSP activity by the addition of 98 μl assay buffer (containing 50 mM sodium acetate, pH 5.2, 80 mM NaCl, 2 mM shikimate-3-phosphate and 2 mM phosphoenolpyruvate), followed by incubation at 37° C. After a specified time interval, the reaction was stopped by the addition of 1.65 ml color reagent (0.87% (w/v) sodium ascorbate, 0.22% (w/v) ammonium molybadate), color was allowed to develop at 45° C. for 20 min., and absorbance was measured at 750 nanometers (nm). Enzyme activity was expressed as nanomole phosphate released per minute per mg protein in the extract.

The levels of isopentyl transferase I (IPTI) were determined as follows. JM101 cells carrying an IPTI expression plasmid were grown in supplemented M9 medium and the recA promoter was induced as described above. Two hours after induction, 1 ml aliquots were taken and the cells recovered by centrifugation. Total cellular proteins were analyzed by non-equilibrium 2-dimensional polyacrylamide gel electrophoresis according to O'Farrell et al. (1977) and the individual proteins were detected by staining with Coomassie Brilliant Blue R250. Stained protein spots were quantiated using a densitometer from Bio-Image ™ (Ann-Arbor, Mich.).

EXAMPLE 1

This example describes the construction and assembly of the synthetic G10L molecule shown in FIG. 1. The synthetic double-stranded DNA (ds DNA) G10L molecule comprises approximately the first 100 base-pair (bp) immediately 5' to the translation start codon (ATG) of the bacteriophage T7 gene 10 coding sequence, and an ATG start codon immediately followed by a G-C bp, with bp substitutions denoted by an underline in FIG. I.

Figures 5A, 5B:
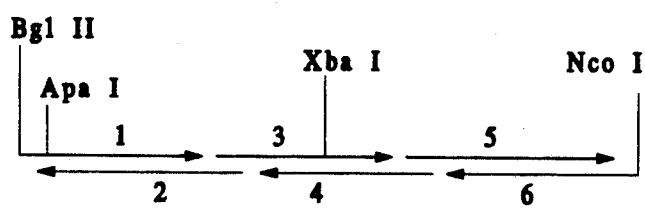
FIG. 5 depicts the construction of the synthetic G10L sequence shown in FIG. 1. Segments #1-#6 denote the individually synthesized oligonucleotides.

In order to produce the ds DNA molecule shown in FIG. 1, six complementary and partially overlapping synthetic oligonucleotides were synthesized as shown in FIG. 5. Aliquots of the crude synthetic oligonucleotides were purified by electrophoresis on polyacrylamide-urea gels, 16% (w/v) in 7M urea. (Maniatis et al., 1982). The concentration of the synthetic DNA in each preparation was determined by quantitative 5'-end labeling reactions using γ-$^{32}$P-ATP at a specific activity of 22,000–24,000 counts per minute (cpm) per mole of ATP, and T4 DNA kinase.

Assembly of synthetic DNA segments 1–6 (FIG. 5) was performed as follows. All six oligonucleotides were phosphorylated at their 5'-ends with polynucleotide kinase. Complementary pairs of oligonucleotides (1, 3, and 5/6) were mixed together in pairs at a concentration of 5 pmol/μl each, in T4 ligase buffer described by the manufacturer. Each pair was then heated to 75° C. for 15 min. and the mixtures were then allowed to cool slowly (i.e. anneal). The three pairs of oligonucleotides were then mixed together and ligated overnight at 15° C. The mixture was then treated with Bgl II and Nco I restriction endonucleases to eliminate any polymers of the G10L that had formed and the assembled G10L fragment was purified by electrophoresis on a non-denaturing 12% polyacrylamide gel (Maniatis et al. 1982). The resultant 104 bp DNA molecules were electroeluted from the gel to yield molecules having the DNA sequence shown in FIG. 1.

EXAMPLE 2

This example describes the construction of various expression vehicles comprising a synthetic G10L molecule operatively joined to heterologous DNA coding sequences. Specifically, expression vectors comprising a synthetic G10L molecule operatively joined to the following DNA coding sequences are described: *E. coli* 3'-enolpyruvyl shikimate 5'-phosphate synthase (EPSP); rat atriopeptigen (APgen); bovine growth hormone (BGH); *Agrobacterium tumefaciens* isopentyl transferase I (IPT I); *E. coli* β-galactosidase (lacZ); *E. coli* chloramphenicol acetyl transferase (CAT); glutathione-S-transferase I (GSTI) and porcine growth hormone (PGH). The following example also describes the construction of otherwise equivalent expression vectors comprising a control ribosome binding site (i.e. SD-sequence) in place of the G10L sequence.

a. EPSP

Figure 6:
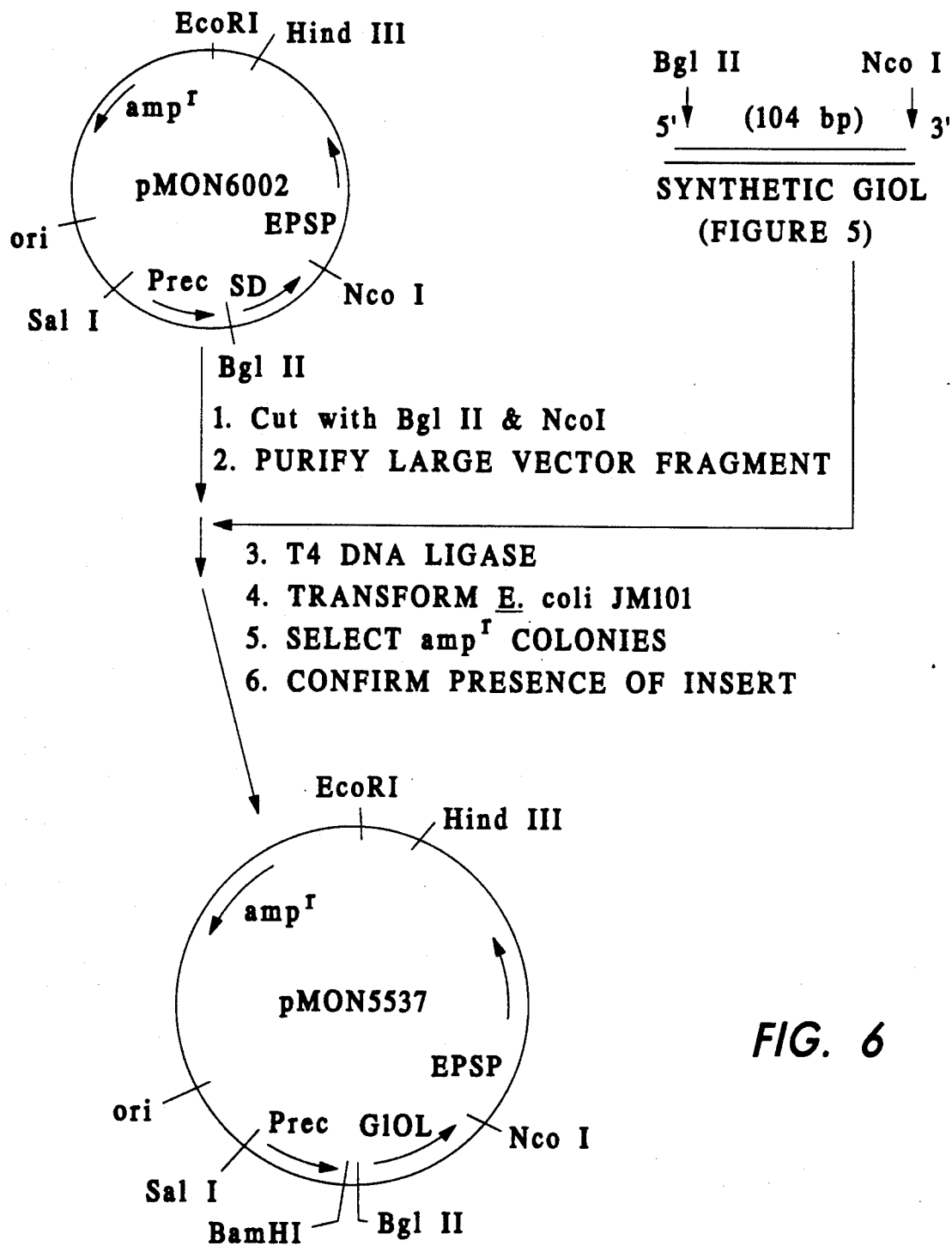
FIG. 6 depicts the construction of the pMON5537 expression vector comprising a recA promoter (Prec), a G10L sequence (G10L) and a 3-enolpyruvyl shikimate 5-phosphate synthase (EPSP) DNA coding sequence.

As shown in FIG. 6, the recombinant expression vector pMON6002 comprising a pBR327 plasmid having inserted therein a recA promoter (Prec), a control SD-sequence (SD) and an *E. coli* EPSP DNA coding sequence (EPSP) was digested (e.g. cut) with restriction endonucleases BglII and NcoI and the large vector fragment was purified by chromatography on NACS resin (BRL, Gaithersburg, Md.) in accordance with manufacturers instructions. Thereafter the vector fragment was mixed with synthetic G10L molecules, obtained as previously described and shown in FIG. 5, in the presence of T4 DNA ligase. Plasmid pMON6002 can be obtained from the ATCC (Rockville, Md.) under ATCC accession number 67044. The resultant pMON5537 vector was then used to transform *E. coli* JM101 cells. Transformed *E. coli* host cells were selected by growth in medium containing 200 μg/ml ampicillin. The creation of expression vector pMON5537 was verified by isolating the expression vector from transformed cells and digesting the isolated vector with restricting enzymes characteristic for the G10L and EPSP sequences.

b. APgen

Figure 7:
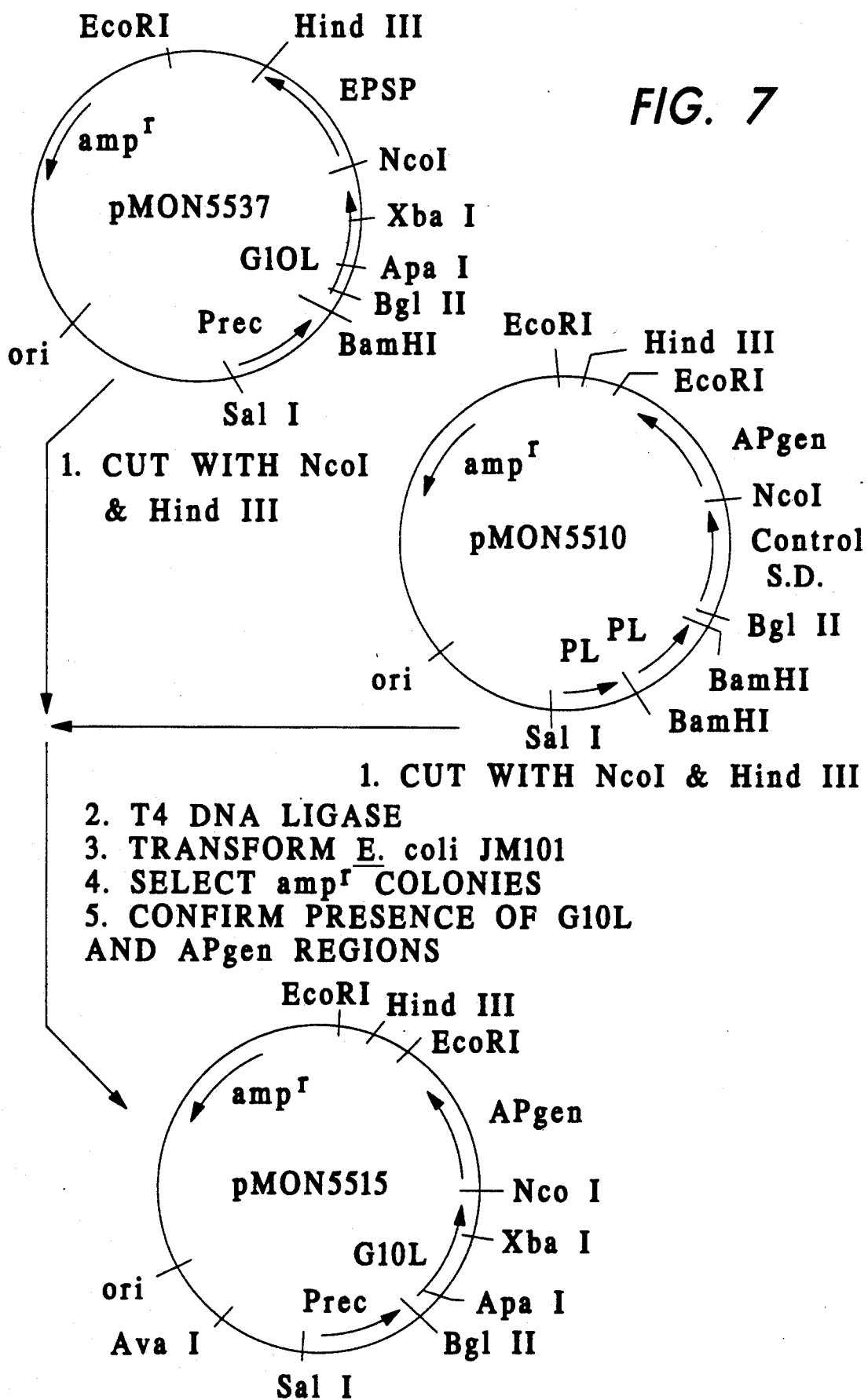
FIG. 7 depicts the construction of the pMON5515 expression vector comprising a recA promoter (Prec), a G10L sequence (G10L) and an atriopeptigen (APgen) DNA coding sequence.

As shown in FIG. 7, the expression vector pMON5510 having ATCC accession No. 67043, comprising a pBR327 plasmid having inserted therein two tandem copies of the $P_L$ promoter ($P_L$), a control SD-sequence (SD) and a DNA coding sequence for rat atriopeptigen (APgen) was digested with Nco I and Hind III and the APgen coding sequence isolated by PAGE. (Maniatis et al. 1982). The APgen coding sequence was then mixed, in the presence of T4 DNA ligase, with pMON5537 which has been previously digested with Nco I and Hind III and treated with calf intestine alkaline phosphatase (CIAP). The resultant pMON5515 vector was then used to transform E. coli JM101 cells and transformants selected by growth on LB agar plates containing ampicillin. Insertion of the APgen DNA coding sequence into the pMON5515 vector was confirmed by digesting the isolated vector with restriction enzymes characteristic for the G10L and APgen sequences.

Figure 11:
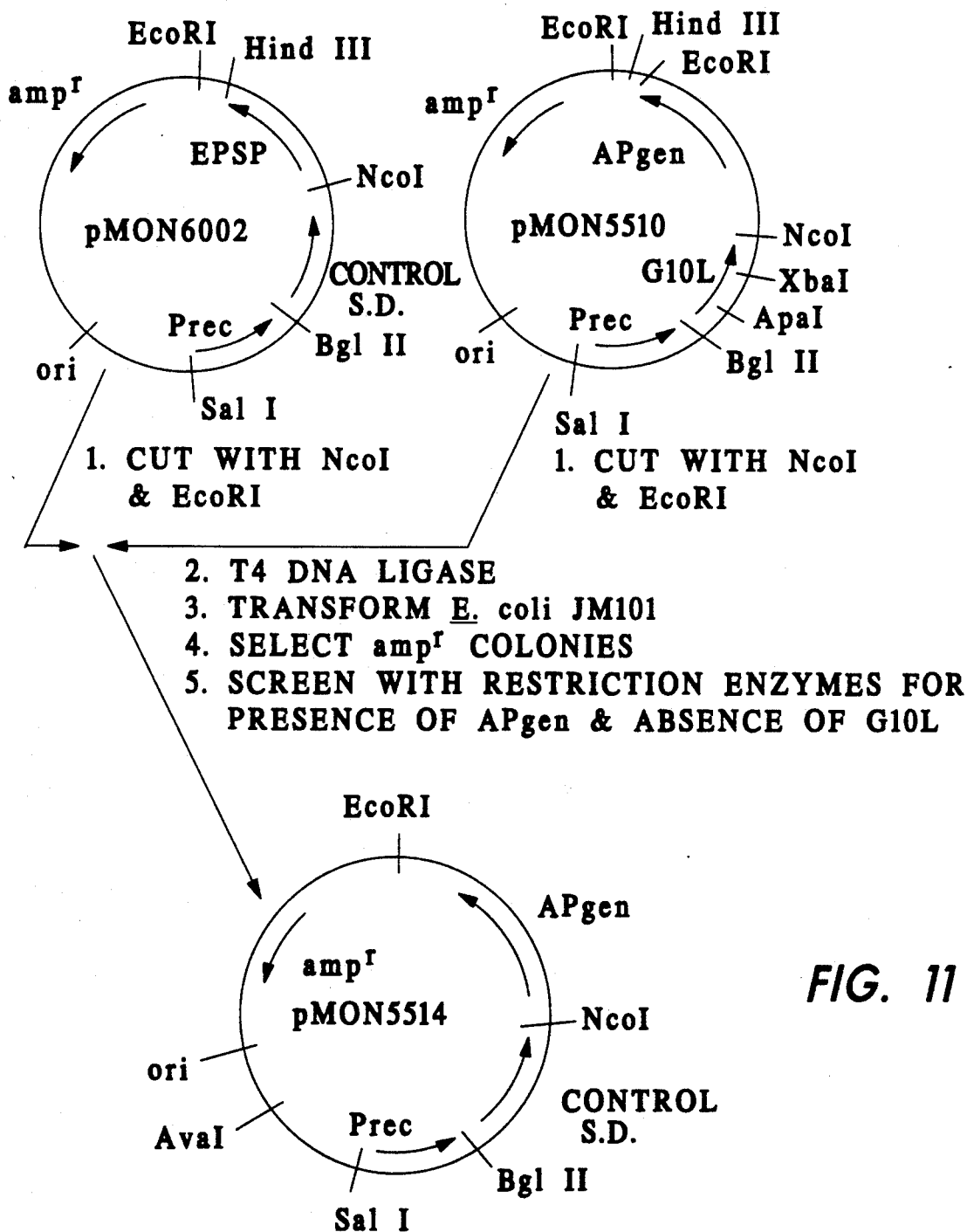
FIG. 11 depicts the construction of the pMON5514 expression vector comprising a recA promoter (Prec), a control R.B.S. (control S.D.) and an APgen coding sequence.

An otherwise identical APgen expression vector containing a control ribosome binding site (R.B.S.) (i.e. SD-sequence) in place of the G10L sequence was constructed as follows. As shown in FIG. 11, plasmids pMON6002 and pMON5515 were individually digested with EcoRI and NcoI and then mixed in the presence of T4 DNA ligase. The ligation mixture was then used to transform E. coli JM101 cells and transformants selected by growth in ampicillin-containing medium. The desired vector, designated pMON5514 containing control R.B.S. (control SD-sequence) operatively joined to the APgen coding sequence was confirmed by digestion with restriction endonucleases showing the absence of a G10L sequence and presence of an APgen coding sequence.

c. BGH

A pBGH$_{ex-1}$ plasmid carrying a DNA coding sequence for BGH was obtained from Genentech, Inc., So. San Francisco, Calif. This plasmid can be prepared as described in European Patent Application publication No. 75,444 (published Mar. 30, 1983); Seeburg et al. (1983); Goeddel et al. (1979); DeBoer et al. (1982); Miozzare and Yanofsky (1978); and Rosenberg and Court (1979). The pBGH$_{ex-1}$ expression vector is a pBR322 bacterial plasmid carrying a gene for BGH [BGH(P)] wherein the N-terminal amino acids of the BGH protein encoded therein are NH$_2$-methionine (met) and phenylalanine (phe). The gene comprises, in sequence, a tryptophan promoter (Ptrp), a segment of 5' non-translated mRNA, translation start codon immediately adjacent to the N-terminal phe (P) codon of BGH, the BGH coding sequence and a translation termination codon.

Figure 8:
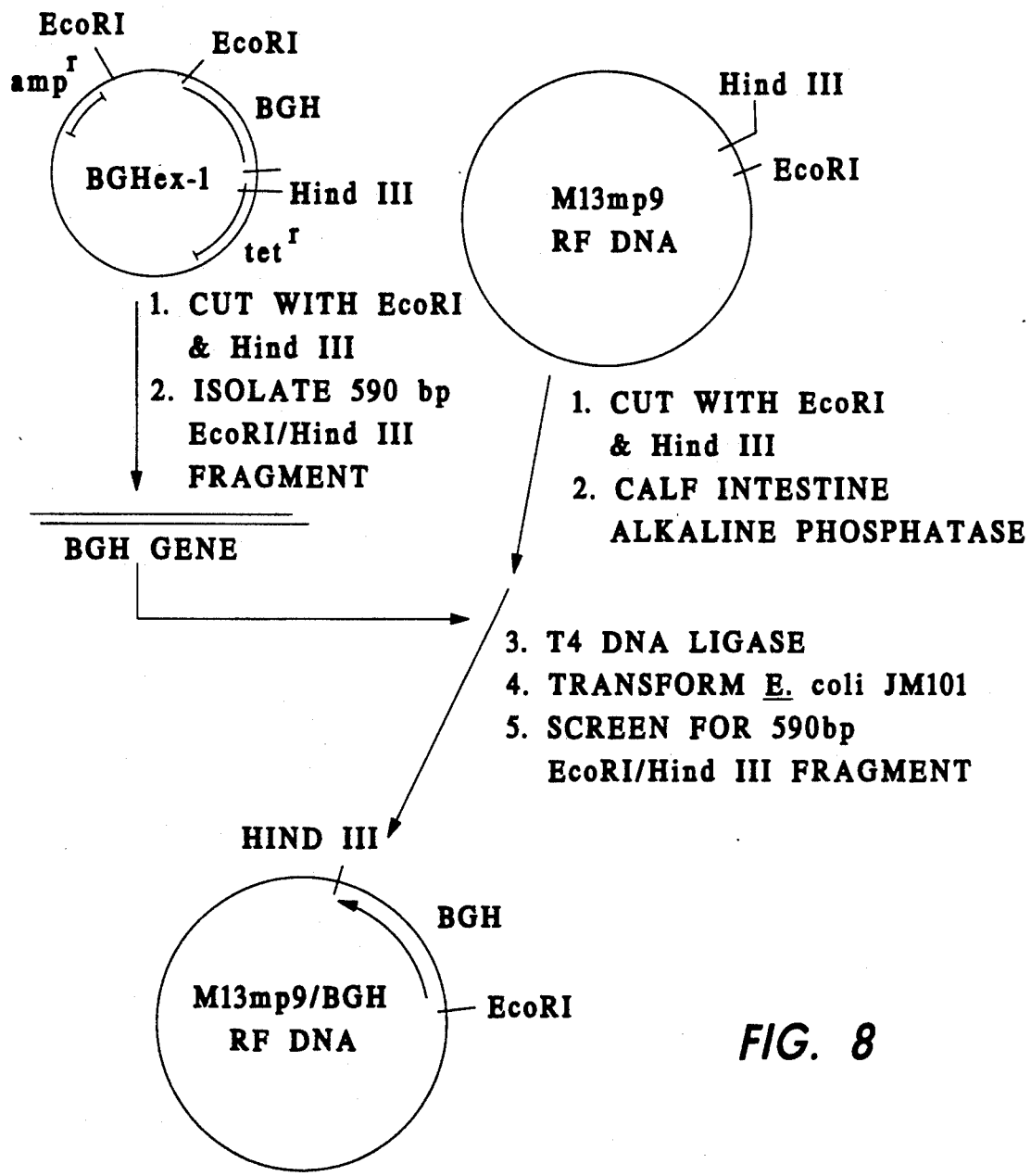
FIG. 8 depicts the construction of M13mp9/BGH comprising M13mp9 replicative form (RF) DNA carrying a bovine growth hormone (BGH) DNA coding sequence.
Figure 9:
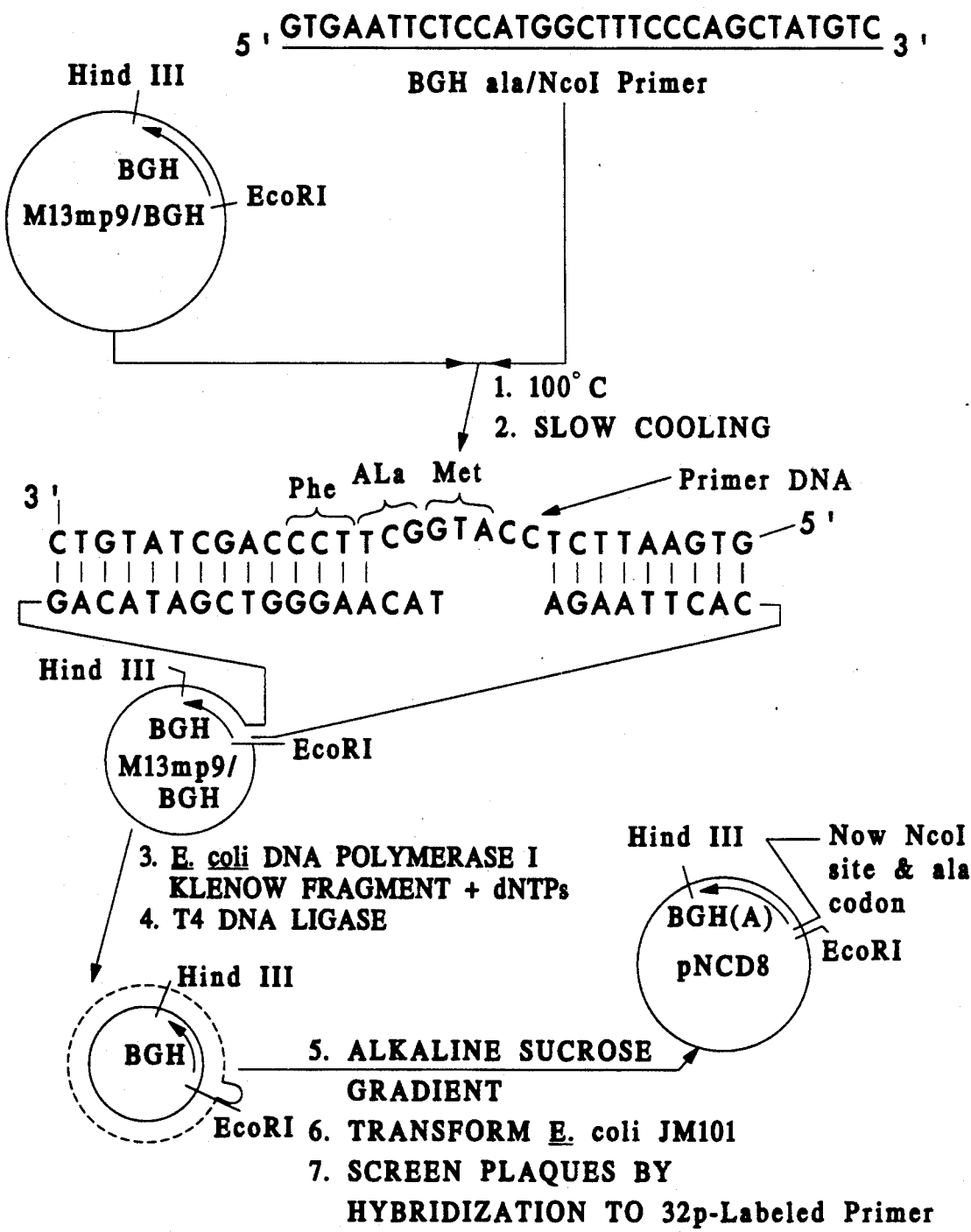
FIG. 9 depicts the creation of a BGH(A) coding sequence from a BGH(P) coding sequence by oligonucleotide-directed site-specific mutagenesis.

As shown in FIGS. 8 and 9, the BGH(P) coding sequence was modified by oligonucleotide-directed site-specific mutagenesis to contain an alanine (ala) codon, immediately preceded by a N-terminal translation start (ATG) methionine codon, and NcoI restriction site overlapping the translation start (ATG) codon as follows. The BGH(P) DNA coding sequence was excised from the plasmid BGH$_{ex-1}$ as a HindIII/EcoRI fragment and cloned into the HindIII/EcoRI site of M13mp9 double-strand DNA (RF DNA). Insertion of the BGH(P) DNA coding sequence into HindIII/EcoRI restricted RF M13mp9 DNA to create recombinant vector M13mp9/BGH, shown in FIG. 8, was initially ascertained by colorless plaque formation on a lawn of bacteria, E. coli JM101 grown in 1×YT medium employing the soft agar overlay procedure described in Maniatis et al. (1982) which included 10 ml 100 mM IPTG (isopropyl-$\beta$-D-thiogalactopyranoside) and 50 $\mu$l 2% (w/v) X-GAL(5-bromo-4-chloro-3-indolyl-$\beta$-D-galacto-pyranoside) in 3 ml of top agar, and transfected with said recombinant vector as described in Maniatis et al. (1982). Insertion of the BGH coding sequence was confirmed by cleavage of RF DNA isolated from colorless plaques, Maniatis et al. (1982), of the recombinant vector with HindIII and EcoRI which yields a 590 bp fragment comprising the inserted sequence. The 590 base pair (bp) fragment was identified by agarose gel electrophoresis in one percent (w/v) agarose as described in Maniatis et al. (1982). All subsequent restriction fragments were identified by this referenced method. The isolation of single-stranded (ss) phage DNA was conducted in accordance with the method of Messing et al. (1982). The M13mp9 BGH vector was then employed as a template in the oligonucleotide-directed site-specific mutagenesis essentially as described by Zoller and Smith (1982), Zoller and Smith (1983), and Norris et al. (1983), the relevant portions of which are herein incorporated by reference.

FIG. 9 diagrams the mutagenesis procedure for creation of a BGH coding sequence [BGH(A)] comprising an N-terminal met codon immediately followed by an alanine codon and NcoI site from the BGH coding sequence having an N-terminal met codon immediately followed by phenylalanine codon [BGH(P)] and lacking an NcoI site. Briefly, an oligonucleotide primer containing the sequence of the desired mutation was used to prime synthesis of a closed-circular DNA copy of the ssDNA M13mp9/BGH template. The sequence of this primer is shown in FIG. 9. The closed-circular dsDNA molecules thus generated are separated from incomplete and ssDNA circles by alkaline sucrose gradient centrifugation as described by Zoller and Smith (1983). The closed-circular dsDNA molecules are then used to transform E. coli JM101 as described by Messing et al. (1982) and the resulting colorless plaques are lifted onto nylon Biodyne TM filters obtained from Pall Ultrafine Filtration Corp. (Glen Cove, N.Y.) and screened for hydridization to a $^{32}$P-labeled form of the oligonucleotide primer used to generate the site-specific mutagenesis. The lifting of said plaques was conducted in accordance with methods described by the Pall Filter manufacturer. Hybridization screening was carried out using nylon Biodyne filters as described by Pall Ultrafine Filtration Corporation (Glenn Cove, N.Y.) in their "Protocol Guide for DNA Transfer to Pall Biodyne TM A Nylon Filters" (1983). Filters were washed at increasing temperatures until the radiolabeled signal was removed from a control filter which was prepared with M13mp8/bGH$_{ex-1}$ phage. A typical filter washing protocol employed a room temperature wash in 6×SSC (0.9M NaCl and 0.09M NaCitrate) for ten minutes followed by a 50° wash in 6×SSC for five minutes and subsequent washings at temperatures increasing by 5° C. Plaques which hybridized to radiolabeled oligonucleotide primer at temperatures higher than the control phages were presumed to carry the newly created BGH(A) coding sequence and were termed potential positives. Alternatively, individual colorless plaques were picked from the *E. coli* JM101 transformations and grown in 5 milliliters (ml) of 2×YT medium comprising (1.6% (w/v) tryptone, 1.0% (w/v) yeast extract and 0.5% (w/v) NaCl, overnight at 37° C. with aeration. Phage DNA, prepared in accordance with Messing et al. (1982) was then spotted onto nitrocellulose, hybridized with radiolabeled primer, and washed in increasing temperatures as described above. Phage DNA which showed hybridization temperatures higher than M13mp9 BGH control plaques were similarly termed potential positives. Potential positive plaques from both screening procedures were grown as described above and used to prepare ss phage DNA, which was then sequenced according to the procedure of Sanger et al. (1977) to confirm that they carried the BGH(A) coding sequence. The resultant recombinant M13mp9 phage DNA containing the BGH(A) coding sequence and NcoI restriction site was denoted pNCD8 (see FIG. 9).

Figure 10:
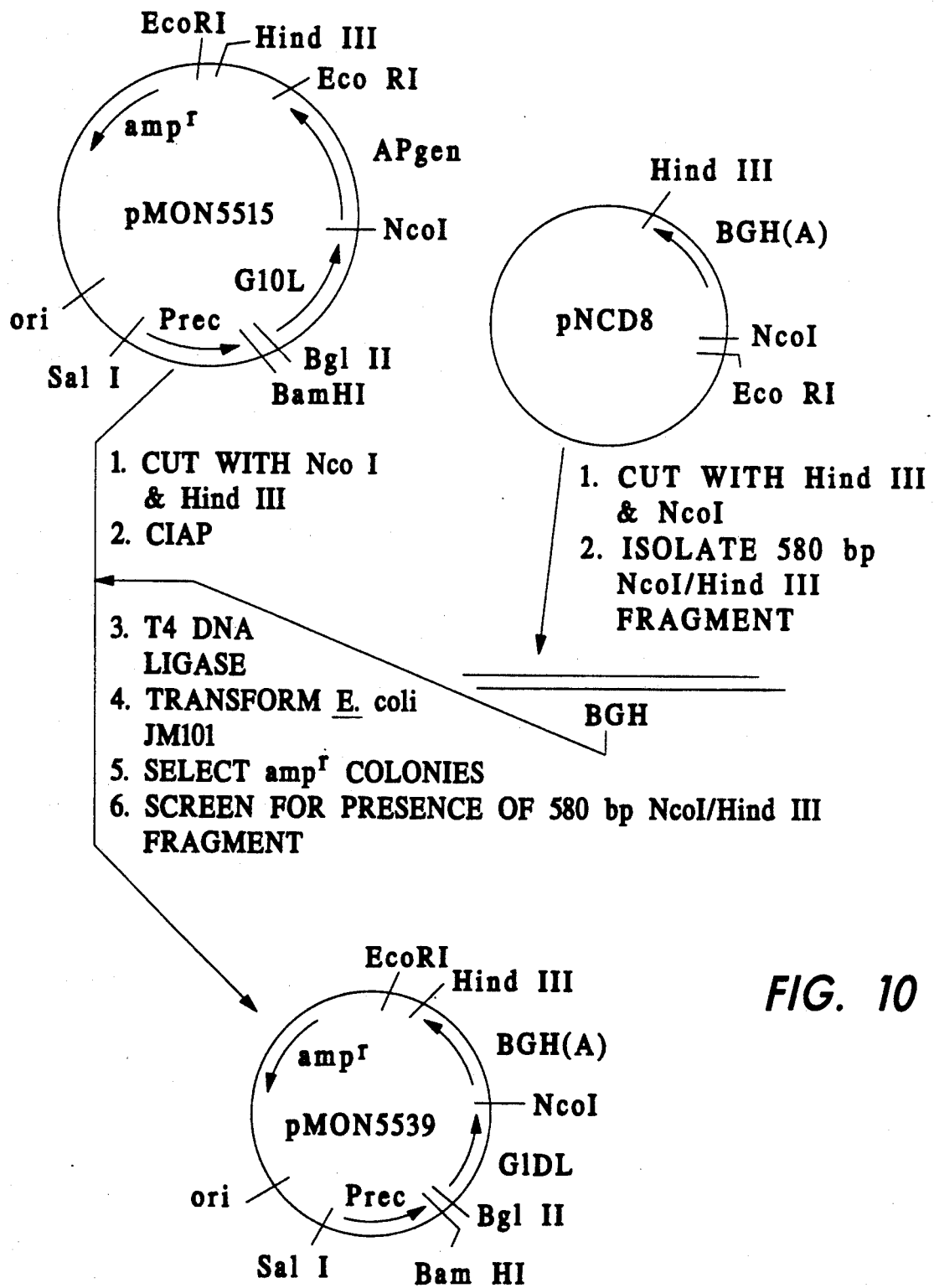
FIG. 10 depicts the construction of the pMON5539 expression vector comprising a recA promoter (Prec), a G10L sequence (G10L) and a BGH(A) coding sequence.

FIG. 10 shows the construction of a pBR327 plasmid comprising a G10L sequence operatively joined to a BGH(A) coding sequence. Specifically, pNCD8 was digested with HindIII and NcoI and the 580 bp DNA fragment containing the BGH(A) coding sequence isolated. The 580 bp DNA fragment was then mixed, in the presence of T4 DNA ligase, with pMON5515 previously digested with NcoI and HindIII and treated with CIAP. The mixture was then employed to transform *E. coli* JM101 and transformants selected by growth in ampicillin-containing medium. The resultant recombinant plasmid comprising a pBR327 plasmid having inserted therein a Prec sequence, a G10L sequence and a DNA sequence coding for BGH(A) was denoted pMON5539 (See FIG. 10).

Figure 12:
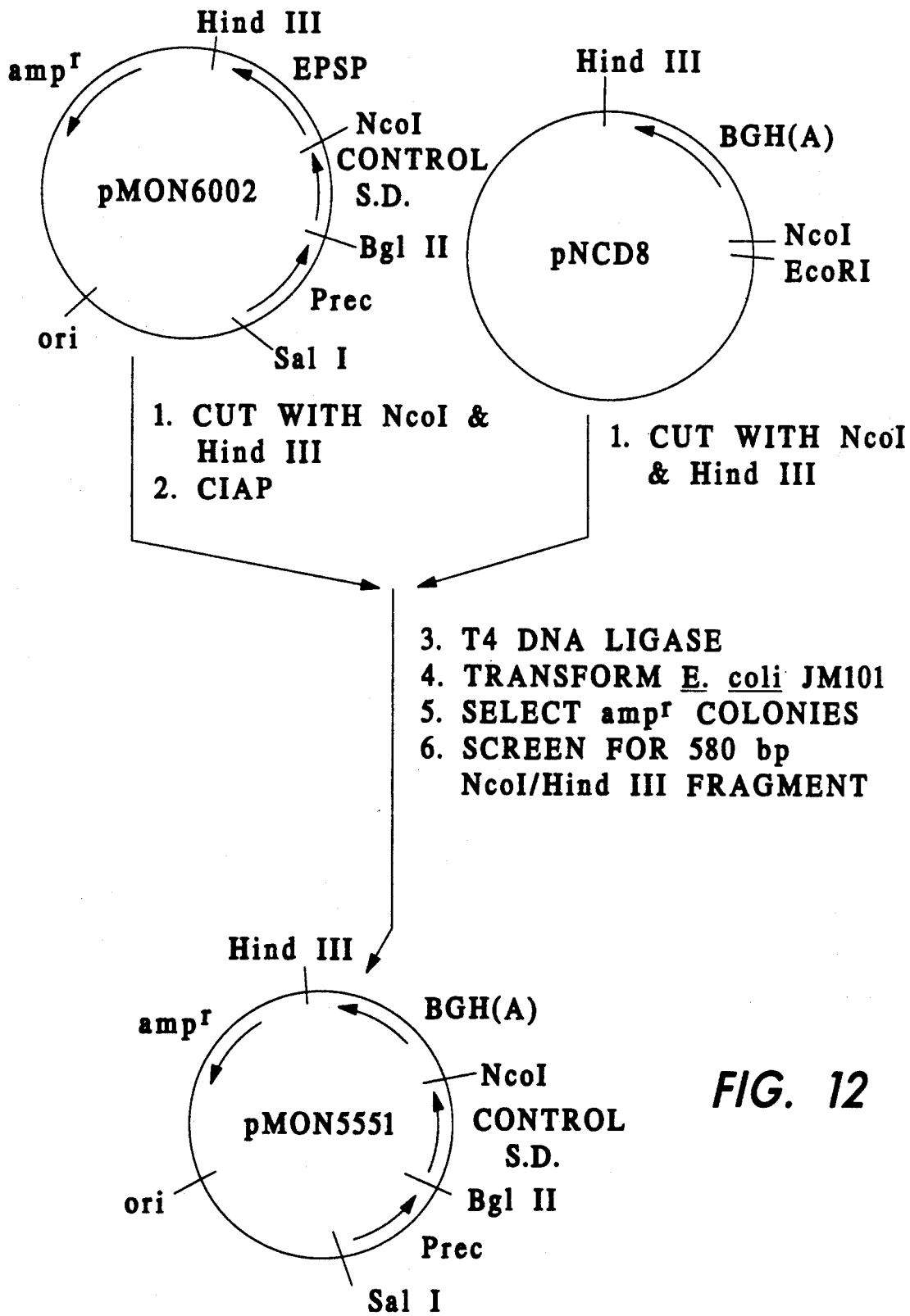
FIG. 12 depicts the construction of the pMON5551 expression vector comprising a recA promoter (Prec), a control R.B.S. (control S.D.) and a BGH(A) coding sequence.

The construction of an otherwise identical expression plasmid containing a control R.B.S. in place of the G10L sequence was carried out as shown in FIG. 12. Plasmid pNCD8 was digested with NcoI and Hind III and mixed, in the presence of T4 NDA ligase, with pMON6002 previously digested with NcoI and Hind III and treated with CIAP. *E. coli* JM101 were then transformed with the resultant plasmids and transformants selected by growth in ampicillin-containing medium. The resultant plasmid, designated pMON5551, comprising a control S.D. sequence operatively joined to a BGH(A) coding sequence was confirmed by digestion with NcoI and Hind III and determining the presence of a 580 bp NcoI/Hind III fragment.

A BGH expression vector was also constructed in accordance with the methods described herein which vector comprised the following sequentially operatively joined: a recA promoter, a G10L sequence, a BGH(A) coding sequence and a transcription "terminator fragment", the latter as more fully described in section "h" of this Example 2, below. This BGH expression vector, designated pMON5557, also carried an ampicillin resistance marker and pBR327 replication origin functions.

d. IPT(I)

Expression vectors for IPT(I) comprising a pBR327 plasmid having inserted therein a recA promoter, a R.B.S. (i.e. G10L sequence or Control R.B.S.) flanked by BglII and NcoI restriction sites, and a DNA sequence coding for IPT I (Goldberg et al., 1984), which coding sequence contained a NcoI site at the start of the coding sequence and a HindIII site downstream of the IPTI coding sequence, were constructed in a manner analogous to the APgen expression vectors. The resulting pair of expression vectors were designated pMON222, which contained a G10L sequence, and pMON5525, which contained the control R.B.S. (control S.D.)

e. CAT

Construction of an expression vector comprising a G10L sequence and DNA coding for CAT was as follows. The sequence of the CAT gene has been described previously by Alton, N. K. and Vapnek, D. (1979). The publication of a DNA sequence encoding a desired protein is sufficient to enable one of skill in the art to synthesize such a coding sequence and/or isolate the coding sequence form DNA libraries by conventional techniques. In order to move this gene into our standard expression vector system, unique restriction sites were created at the start of the gene (NcoI) and downstream of the gene (EcoRI), using oligonucleotide-directed site-specific mutagenesis. These restriction sites are compatible with the two expression vectors pMON5515 and 5514 (containing the G10L and control S.D., respectively). An NcoI/EcoRI fragment containing the CAT DNA coding sequence can be isolated and inserted into the corresponding restriction sites of pMON5515 and pMON5514 as previously described in place of the DNA sequence coding for APgen. The resulting two plasmids would be identical, consisting of a pBR327 plasmid having inserted therein a recA promoter, a R.B.S. (either G10L or control SD-sequence) and the CAT DNA coding sequence. The examples used for the comparison of the efficacy of the two R.B.S sequences had, in addition, an extra segment of DNA downstream of the CAT coding sequence. This segment consisting of a small fragment of M13 phage containing the origin of replication. This segment was the same for both CAT DNA-containing constructs (containing the G10L or control S.D.), and should not influence the relative efficiencies of the two R.B.S. sequences.

The final constructed expression plasmid comprising a control SD-sequence operatively joined to a CAT DNA coding sequence was designated pMON5600. The final constructed expression plasmid comprising a G10L sequence operatively joined to a CAT DNA coding sequence was designed pMON5582.

f. lacZ

Construction of an expression vector comprising a G10L sequence operatively joined to DNA coding for lacZ was as follows. Plasmid pNM480 was obtained from N. Minton (Public Health Laboratory Service, Porton Down, Salisbury, U.K.) and is described by Minton, N. P. (1984). Briefly, pNM480 comprises a pBR322 derivative plasmid having inserted therein the lac operon of *E. coli* starting at the start of the lacZ coding region. The pNM480 plasmid was digested with Nco I which cuts at the extreme 3' end of the lac operon. This site was then destroyed by filling in the sticky ends with Klenow fragment of DNA polymerase I and religating the DNA. The resulting plasmid was screened for the loss of the Nco I site and designated pMON5526. The previously described pMON5515 plasmid was used as a source of recA promoter and G10L elements. Specifically, pMON5515 was digested with Ava I and Nco I and the smaller fragments was isolated by preparative agarose gel electrophoresis. The ends of the fragment were then rendered blunt by treatment with the Klenow fragment of DNA polymerase I. pMON5526 was then cleaved at the unique Sma I site contained in a multilinker at the start of the lacZ coding region and the prepared fragment from pMON5515 was ligated thereto. The resulting plasmid, pMON5527, had the desired orientation, namely it had the recA promoter and G10L immediately upstream of an Nco I site at the start of the lacZ coding region.

The construction of an otherwise identical expression plasmid containing the control R.B.S. in place of the G10L sequence can be carried out as described previously for the APgen expression plasmids. The resultant plasmid, designated, pMON5540, comprised a recA promoter, the control R.B.S. and DNA coding for the lacZ protein.

g. GSTI

Expression vectors for GSTI were constructed analogous to those for APgen, in that they comprised a pBR327 plasmid having inserted therein a recA promoter, a R.B.S. sequence (i.e. G10L sequence or control R.B.S. sequence) flanked by BglII and NcoI sites, an NcoI site at the start of the coding region for GSTI, a GSTI coding sequence and an EcoRI site downstream from the GSTI coding sequence. The 642 base-pair maize GSTI coding sequence can be isolated by conventional means based upon the following partial GST peptide sequence:

$$\text{NH}_2\text{-valine}^9\text{-methionine}^{10}\text{-serine}^{11}\text{-tryptophan}^{12}\text{-asparagine}^{13}\text{-valine}^{14}\text{-COOH}$$

wherein the superscript numerals indicate the position of the specified amino acid in the 214 amino acid GSTI protein. The resulting pair of plasmids were pMON2054, which contains the control R.B.S. and pMON5541 which contains the G10L sequence.

h. PGH

Expression vectors for PGH containing either a G10L or control SD-sequence were constructed as follows. A pUC18 plasmid was cleaved with EcoRI and SalI to isolate a pUC18 DNA segment having the following sequence:

```
EcoRI              SmaI              SalI
 |                  |                 |
5'-AATTCGAGCTCGGTACCCGGGGATCCTCTAGAG-3'
      GCTCGAGCCATGGGCCCCTAGGAGATCTCAGCT
```

The pUC18 DNA segment was then ligated to a T7 gene 10 terminator having the following sequence:

```
XhoI                                                    EcoRI
 |                                                       |
5'-TCGAGCATAACCCCTTGGGGCCTCTAAACGGGTTGAGGGGTTTTTTGCTG-3'
      CGTATTGGGGAACCCCGGAGATTTGCCCAGAACTCCCCAAAAAACGACTTAA
```

The SalI restriction end of the pUC18 DNA segment can base-pair with the XhoI restriction end of the terminator sequence destroying both the SalI and XhoI sites. The ligation thus results in formation of an 86 bp fragment having EcoRI sites at both its 3'- and 5'-ends. This 86 bp DNA fragment was designated a "terminator fragment."

Multiple copies of the terminator fragment were generated by insertion of said fragment into the EcoRI site of the pUC18 plasmid which created a recombinant plasmid designated pMON2318. pMON2318 was then replicated in *E. coli* JM101 grown in media containing ampicillin as previously described.

The terminator fragment was then inserted into pMON5539 (see Section C, above) as follows. pMON2318 was isolated and digested with EcoRI and the 86 bp DNA fragment was then mixed, in the presence of T4 DNA ligase, with pMON5539, previously digested with EcoRI, to create a resultant plasmid designated pMON5557. Plasmid pMON5557 comprised the following components sequentially operatively joined: a recA promoter, a G10L sequence, a BGH(A) coding sequence and a terminator fragment. pMON5557 also contained an ampicillin resistance marker.

A DNA sequence coding for a PGH(A) protein (e.g. a porcine growth hormone protein containing an N-terminal alanine) was then inserted into pMON5557 in place of the BGH(A) coding sequence as follows. An NcoI restriction site was introduced at the 5'-end of the PGH(A) coding sequence carried in pMON3213 by oligonucleotide-directed site-specific mutagenesis. pMON3213 can be obtained from the ATCC under accession number 53023 and is described in European Patent Application publication number 193,515 (published Sep. 9, 1986) incorporated herein by reference. Specifically, pMON3213 was cleaved with EcoRI and HindII and a resulting 590 bp fragment isolated and inserted into M13mp19. The resulting recombinant M13mp19 DNA was passaged twice through *E. coli* strain BW313 according to the procedure of Kunkel (1985) in order to incorporate uracil residues at a portion of the thymidine positions in the recombinant M13mp19 DNA. Single-stranded DNA forms of the recombinant M13mp19 DNA were isolated in accordance with the method of Messing et al., (1982) and employed as templates in the oligonucleotide-directed site-specific mutagenesis as described by Zoller and Smith (1982, 1983) and Norris et al., (1983). In vitro synthesis of the homologous DNA strand was primed with the following 27-base oligonucleotide primer, sequence:

```
EcoRI              NcoI
                met ala phe pro
CAGTGAATTCTCCATGGCCTTCCCAGC
```

Following second (e.g. homologous) strand synthesis, the DNA was inserted into a wild-type *E. coli* strain, JM101, to enrich for plaques containing the mutated DNA.

Four clear plaques resulted from the insertion of the mutated DNA into the wild-type *E. coli* JM101. the plaques were selected and grown overnight in 2×YT medium at 37° C. Single-stranded DNA was prepared and sequenced by the dideoxy-chain termination method of Sanger et al. (1977). Two of four DNA's sequenced contained the NcoI site. Presence of the additional restriction site was also confirmed by NcoI digestion. The PGH(A) gene with the NcoI at the 5'-end, cloned in M13mp19, was designed pMON3267.

The PGH(A) DNA coding sequence was then isolated as an NcoI/HindIII fragment following digestion of pMON3267 with NcoI and HindIII. The PGH(A) DNA coding sequence was then mixed, in the presence of T4 DNA ligase, with pMON5557 previously digested with NcoI and HindIII. The resultant plasmid, designated pMON5647, was then employed to transform E. coli JM101 which were grown in ampicillin containing medium to select for transformants. pMON5647 contained the following DNA segments sequentially operatively linked: a recA promoter, a G10L (e.g. 104 bp) sequence, a PGH(A) coding sequence and a terminator fragment.

An otherwise identical PGH(A) expression vector containing a control R.B.S. (e.g. control SD-sequence) in place of the G10L sequence was constructed as follows. Plasmid pMON5551, described previously and shown in FIG. 12, was cleaved with NcoI and PstI and the DNA fragment carrying the plasmid origin of replication (ori), recA promoter (Prec) and control SD-sequence was purified and mixed, in the presence of T4 DNA ligase, with an NcoI/PstI fragment carrying the PGH(A) and terminator sequences purified from a pMON5647 plasmid previously digested with NcoI and PstI. The ligation mixture resulted in formation of recombinant plasmid designated pMON5715 comprising the following DNA segments sequentially operatively joined: recA promoter, a control R.B.S., a PGH(A) coding sequence and a transcription termination sequence. Plasmid pMON5715 also contained a ampicillin resistance marker and replication origin functions of plasmid pBR327.

EXAMPLE 3

This example describes a comparison of the accumulation of a variety of proteins produced in E. coli using expression vectors containing either a G10L sequence or a control R.B.S. (e.g. control SD-sequence).

E. coli JM101 or W3110 cells were transformed with one of the following expression vectors: pMON6002, pMON5537, pMON5540, pMON5527, pMON5600, pMON5582, pMON5541, pMON2054, pMON5551, pMON5539, pMON5514, pMON5515, pMON5647 or pMON5715, the constructions of which are described in Example 2, above. Protein production was assayed as follows. Protein-specific enzyme activity was measured for EPSP, lacZ, CAT and GSTI as previously described. Protein accumulation of BGH and APgen were measured by Western immunoblotting as previously described. IPT I accumulation was determined by densitometry of a stained protein gel as previously described. PGH accumulation was determined by visual inspection of total cell protein stained with Coomassie Brilliant Blue following separation on a 15% (w/v) sodium dodecyl sulfate polyacrylamide gel (see Laemmli, 1970).

As shown in Table I, below, expression plasmids containing a G10L sequence significantly enhanced protein accumulation for all proteins produced. A preferred enhancement in protein accumulation was achieved for BGH, APgen, IPT I, GST I and lac Z and a most preferred enhancement achieved for BGH and IPT I.

TABLE I

| | Relative Protein Accumulation | |
|---|---|---|
| | Ribosome Binding Site | |
| Gene | Control SD-Sequence | G10L Sequence |
| BGH | 1 | 400 |
| APgen | 1 | 50 |
| IPT I | 1 | 340 |
| GST I | 1 | 100 |
| lac Z | 1 | 100 |
| CAT | 1 | 1.6 |
| EPSP | 1 | 12 |
| PGH | 1 | 7 |

EXAMPLE 4

This example describes the effect of different promoters on the accumulation of proteins produced in E. coli host cells using expression vectors containing a G10L sequence.

Expression vectors comprising a G10L sequence and a BGH or APgen DNA coding sequence operatively joined to a recA, tryptophan (trp) or $P_L$ promoter were constructed. The construction of expression vectors comprising a recA promoter, a G10L sequence and an AP gen or both DNA coding sequence was as described above in Example 2. Otherwise equivalent expression vectors comprising either a trp or $P_L$ promoter in place of the recA promoter can be constructed, briefly, as follows. Both the trp and $P_L$ promoters described in Rosenberg and Court (1979), can be chemically synthesized by conventional means. Alternatively the trp promoter can be isolated from plasmid $pBHG_{ex-1}$, described by Seeburg et al. (1983), and the $P_L$ promoter can be isolated from pMON5510 which has been deposited with the ATCC and has been given ATCC accession No. 67043. A SalI site can the be inserted at the 5'-end of the promoter sequence by conventional means and a BamHI site similarly inserted at the 3'-end of the promoter sequence. The trp or $P_L$ promoter sequence can then be inserted into the pMON5515 or pMON5539 plasmids in place of the recA promoter in accordance with previously described methods. By such means, expression vectors comprising a trp promoter, a G10L sequence and BGH coding sequence or comprising a trp promoter, a G10L sequence and an APgen coding sequence, or comprising a lambda $P_L$ promoter, a G10L sequence and a BGH coding sequence, or comprising a $P_L$ promoter, a G10L sequence and an APgen coding sequence were constructed. E. coli JM101 or W3110 were then transformed with one of the expression vectors and the levels of BGH and APgen accumulation determined as previously described.

As shown in Table II, below, essentially equivalent enhancement of protein accumulation was achieved with a variety of promoters operatively joined to the G10L sequence and BGH or APgen coding sequence. The preferred promoters for the expression vectors employed to produce BGH or APgen in E. coli were determined to be the recA and trp promoters.

TABLE II

| Effect of Different Promoters on Protein Accumulation** | | |
|---|---|---|
| | GENE | |
| Promoter* | Atriopeptigen | Bovine Growth Hormone |
| recA | +++ | +++++ |
| tryptophan | +++ | +++++ |

TABLE II-continued

Effect of Different Promoters on Protein Accumulation**

| | GENE | |
|---|---|---|
| Promoter* | Atriopeptigen | Bovine Growth Hormone |
| Lambda P$_L$ | +++ | ++++ |

*all promoters were operatively joined to a G10L sequence contained within an expression vector.
**the (+)s denote relative levels of accummulation as measured by protein staining of SDS-polyacrylamide gels as previously described.

EXAMPLE 5

This example describes the construction of an expression vector comprising the G10L sequence shown in FIG. 2 which was found to enhance protein production in bacteria to essentially the same level as an expression vector comprising the G10L sequence shown in FIG. 1.

Expression vector pMON5515 was digested with restriction enzymes ApaI and XbaI. The plasmid ends were then rendered flush (blunt) by incubation, at room temperature, with E. coli DNA polymerase I, Klenow fragment, in the presence of all four deoxynucleoside triphosphates (dNTPs), at a concentration of 250 µM each. After incubating for 5 minutes at room temperature, all enzymes were inactivated by the addition of one tenth volume of diethyl pyrocarbonate (an aqueous solution in 60% (v/v) ethanol). The diethyl pyrocarbonate was thereafter destroyed by heating at 65° C. for 5 minutes. The plasmid was then re-ligated with T4 DNA ligase. By these means, bases 8 through 59 (FIG. 1) of the G10L sequence contained within pMON5515 from the ApaI site to the XbaI site was deleted yielding an expression vector, designated pMON5521, comprising a G10L shown in FIG. 2. E. coli JM101 host cells were transformed with either pMON5515 or pMON5521. the levels of APgen produced in the E. coli cells so transformed were then determined, as previously described, and were found to be essentially equivalent when either the G10L sequence shown in FIG. 1 or 2 were employed.

EXAMPLE 6

This example demonstrates that G10L sequences as short as 7 or 9 nucleotides in length can be employed to effect enhanced protein production in bacteria. Additionally, this example demonstrates that G10L sequences can be inserted at various positions within a gene and still cause enhanced desired heterologous protein accumulation in bacteria.

The G10L sequences employed in this Example 6 comprised a DNA equivalent of the G10L 16S rRNA homology sequence identified in FIG. 3 or a fragment thereof. Specifically, G10L sequences containing one of the following sequence of nucleotides were employed:
5'-TTAACTTTA-3', or
5'-AACTTTA-3', or
5'-TTAACTT-3' a. In order to demonstrate that said sequences can enhance heterologous protein production in bacteria, expression vectors were constructed which differed only in the presence or absence of a G10L sequence. For example, a GSTI expression vector containing a control SD-sequence and an otherwise identical GSTI expression vector containing a G10L 16S rRNA homology sequence just upstream from the control SD-sequence were compared for their respective abilities to effect GSTI production in E. coli. The B10L containing GSTI vector contained the following synthetic sequence:

5'-GATCTTTTAACTTTAGTAAGGAGTCTAGAC-3'
    AAAATTGAAATCATTCCTCAGATCTGG<u>TAC</u> wherein the asterisks (*) denote the G10L 16S rRNA homology sequence, the daggers (†) denote the SD-sequence and the ATG initiator codon is denoted by the underlined nucleotides. The above synthetic double-stranded DNA sequence was constructed so as to contain a BglII site at one end and a NcoI site at the other end so that said sequence could be inserted into the GSTI gene in accordance with the methods previously described herein. E. coli transformed with one of these GSTI expression vectors were then assayed for GSTI protein production as previously described. The results of the GSTI production assays showed a 20 fold increase in GSTI produced in E. coli transformed with the G10L 16S rRNA homology sequence containing vector as compared to E. coli transformed with an otherwise identical GSTI expression vector lacking the G10L 16S rRNA homology sequence.

b. A GSTI expression vector containing the control SD-sequence was also employed to demonstrate the ability of a short, 7 nucleotide, G10L sequence to enhance heterologous protein production in bacteria when located within the spacer region (e.g. between the SD-sequence and ATG start/signal codon). Specifically, a GSTI expression vector containing a control SD-sequence was compared to an otherwise identical GSTI expression vector containing the following G10L sequence in the spacer region:
5'-AACTTTA-3'
This G10L sequence represents a fragment or portion of the G10L 16S rRNA homology sequence. Insertion of the foregoing G10L sequence into the GSTI expression vector was accomplished by synthesizing the following synthetic dsDNA fragment:

5'-GATCTTGTAAGGAGAACTTTA-3'
    AACATTCCTCTTGAAATG<u>TAC</u> wherein the daggers denote the control SD-sequence the asterisks denote the G10L 16S rRNA homology fragment and the underlined nucleotides denote the translation start/signal codon. This synthetic ds DNA fragment was then inserted into the GSTI expression vector utilizing the BglII and NcoI ends on the fragment in accordance with methods previously described herein. E. coli transformed with the G10L containing GSTI expression vector showed a 240-fold greater accumulation of GSTI than E. coli transformed with otherwise identical GSTI expression vectors lacking the G10L sequence.

c. A lacZ expression vector was employed to demonstrate that a G10L sequence can enhance heterologous protein production in bacteria when inserted within the coding sequence (e.g. part of the R.B.S.) for the heterologous protein. The previously described (see Example 2, above) lacZ expression vectors have a unique NcoI restriction site at the translation start/signal ATG codon and a unique HindIII site a few bases downstream (e.g. within the lacZ coding region). This NcoI to HindIII region of the lacZ expression vectors can be removed and replaced with a synthetic dsDNA fragment containing a G10L sequence. Specifically, a G10L sequence:

5'-TTAACTT-3' was inserted into a previously described lacZ expression vector by first creating the following synthetic ds DNA fragment:

```
    NcoI          •••••••         HindIII
     |                               |
5'-CATGGGGTTAACTTAAGCTGCAGCCA-3'
    CCCAATTGAATTCGACGTCGGTTCGA
``` wherein the underlined nucleotides denote the translation start/signal codon and the asterisks denote the G10L sequence. This synthetic dsDNA G10L containing fragment was then inserted into a lacZ expression vector in accordance with methods hereinbefore described. E. coli were then transformed, as previously described, with either a lacZ expression vector containing the synthetic dsDNA containing the G10L sequence or an otherwise equivalent lacZ expression vector lacking a G10L sequence. β-galactosidase production by said transformed E. coli was then measured, as previously described. Thus it was determined that E. coli transformed with a G10L sequence containing lacZ expression vector have a 50-fold greater level of β-galactosidase production than E. coli transformed with lacZ expression vectors lacking a G10L sequence.

The foregoing comparisons clearly demonstrate that G10L sequences can be positioned at various regions within the R.B.S. and effectively enhance heterologous protein production in bacteria. These examples also demonstrate that G10L sequences 7 nucleotides in length can effectively enhance heterologous protein production in bacteria. Thus, in accordance with methods herein previously described, sequences were constructed which will enhance protein production in bacteria by promoting mRNA binding or interaction with 16S rRNA.

EXAMPLE 7

This example demonstrates an ability to further enhance heterologous protein production in bacteria by employing a transcription terminator sequence in combination with a G10L sequence. As previously discussed, transcription terminator sequences can be selected from those found in the DNA of the bacterial host chosen to produce the heterologous protein and/or selected from those found in bacteriophage able to infect bacterial host cells.

In the present example, four different transcription terminator sequences were synthesized and inserted into previously described expression vectors containing a G10L sequence. The transcription terminator sequences selected included:

(1) T4gene 23 terminator comprising the following sequence of nucleotides:

5'-AATTCGATATCAAACACAATTTAGG-
  GAACCTTCGGGTTCCCTTTTTCTATTTTC-3'

(2) P22 gene ant terminator comprising the following sequence of nucleotides:

5'-AATTCGATATCAACGCAACGACC-
  CAGCTTCGGCTGGGTTTTTTTGACC-3'

(3) ColE1 terminator comprising the following sequence of nucleotides:

5'-AATTCGATATCGAGCTTTAACAACCGG-
  CCACCGCGCCGGGTTTTTTTGTGCCC-3'

(4) T7 gene 10 terminator comprising the sequence of nucleotides described in Example 2(h), above.

These transcription terminator sequences were synthesized by conventional means and inserted into pMON5539, a BGH expression vector (see Example 2 above) in accordance with conventional methods analogous to those describing the construction of PGH vectors pMON5647 and pMON5715 (see Example 2). E. coli transformed with BGH expression vectors containing a G10L sequence in combination with an above transcription termination sequence gave a range of between 2 and 4 fold enhancements in BGH production, measured as previously described, as compared to E. coli transformed with pMON5539 (an otherwise identical BGH expression vector lacking a transcription terminator sequence).

In another experiment, the synthetic terminator sequence set forth in Example 2, above, was inserted by conventional means into the previously described APgen expression vector pMON5515. Specifically, the synthetic terminator sequence was cloned by conventional means, downstream of the APgen coding sequence and the resultant expression vector was found to cause an about 2 to 3 fold increase in APgen production as determined by visual inspection of a protein stained sodium dodecyl sulfate polyacrylamide gel.

Thus, by combining a G10L sequence with a transcription terminator, heterologous protein production in bacteria can be increased to levels greater than protein production levels achieved by use of a G10L sequence alone.

EXPANDED DISCLOSURE

FIG. 13 depicts the construction of pMON5542 comprising a pEMBL plasmid having inserted therein prec, G10L and a LacZ structural gene.

FIG. 14 depicts the construction of two broad host range expression vehicles, pMON5757 and pMON5758, each comprising an IncQ replicon (IncQ), a gentamicin resistance selectable marker gene (Gm$^r$), prec, a G10L sequence and a beta-galactosidase structural gene (LacZ).

FIG. 15 depicts the relevant contents of plasmids pMON5014, pMON5756, pMON5759, pMON5760 and pMON5761.

As previously discussed, the present invention relates to DNA sequences useful in enhancing protein production in such Gram-negative bacteria as E. coli. This expanded disclosure describes the ability these sequences to cause enhanced protein production in a wide range of Gram-negative genera including, but not limited to, Pseudomonas, Serratia, Erwinia, Proteus, Xanthomonas, Rhizobium, Agrobacterium, Bradyrhizobium, Citrobacter, Salmonella, Vibrio, Aeromonas, Zymomonas, Flavobacterium, Alcaligenes, Enterobacter, Klebsiella and Gluconobacter.

Owing to a need to develop commercially viable expression systems in Gram-negative microorganisms other than E. coli, expression vectors containing G10L sequences operably linked to a promoter and DNA sequence encoding a desired peptide are constructed. As is shown hereinafter, the constructed expression vectors, containing a G10L sequence, are employed to transform heterologous (e.g. non-E. coli) Gram-negative bacteria to cause such transformed bacteria to produce enhanced levels of desired protein. In one embodiment, this enhanced production of desired protein is demonstrated relative to an *E. coli* consensus ribosome binding site, which site is previously described above.

The ability of G10L sequences to function as a ribosome binding site and, further, to enhance desired protein production in heterologous bacteria is significant. For Gram-negative bacteria other than *E. coli*, very little information is available on the structure and function of their respective promoters and ribosome binding sites. Thus, the development of such organisms as host cells for recombinant DNA production of commercially and economically valuable substances has been impeded or, at best, limited.

As shown hereinafter, G10L sequences not only provide functional ribosome(s) binding site(s) but can significantly enhance desired protein production in a wide range of Gram-negative bacteria. As previously discussed, it is anticipated that the G10L sequences of the present invention can function as a ribosome binding site and/or effectively enhance desired protein accumulation when operatively joined to any promoter sequence recognized by the host cell containing such sequences in their genome.

In a preferred embodiment for non-*E. coli* Gram-negative bacteria, enhanced protein accumulation is achieved by operatively joining a G10L sequence to an *E. coli* recA promoter (prec). Additional embodiments of such combinations are described in a co-pending U.S. patent application by D. J. Drahos et al. entitled "Regulated Gene Expression in Gram-Negative Microorganisms", attorney docket number 07-21(487)A, commonly assigned to Monsanto Company, which application is hereby incorporated by reference herein.

Expanded Materials and Methods

*E. coli* JM101, *Pseudomonas testosteroni* and *Serratia marcescens* may be obtained from the American Type Culture Collection (ATCC) (Rockville, Md.) under ATCC accession numbers 33876, 17459 and 25419, respectively. *Pseudomonas putida* mt-2 may be obtained from M. Bagdasarran (Max Plank Institute for Molecular Genetics, D-1000 Berlin-Deblin, F.R.G.) and is described by Murray, K. et al. Eur. J. Biochem. (1972) 28: 301-310. *Psuedomonas aeruginosa* 2003 was obtained from M. Vasil (Univ. Colorado Med. School, Denver, Colo.) and is described by Vasil, M. L. et al. J. Bacteroil (1982) 152: 431-440. *Pesudomonas syringae* JL2000 may be obtained from J. Loper (Dept. Botany and Plant Pathology, Oregon State University, Corvallis, Oreg. 97331) and is described by Loper, J. E. et al. J. Gen. Microbiol, (1984) 130: 1507-1515. *Erwinia herbicola* #26 may be obtained from the collection of A. Kelman (University of Wisconsin, Madison, Wis.). *Pseudomonas fluorescens* 701 E1 is of the type described by D. Drahos et al. biotechnology (1986) 4: 439-444. *E. coli* strain W3110 can be obtained form the ATCC (Rockville, Md.) under ATCC accession number 39936. *E. coli* strain N6405 or obtained from Dr. M. Gottesman, National Institutes of Health (Bethesda, Md.) and can be obtained from the ATCC under accession number 53469. *E. coli* strain BW313 can be obtained from Dr. Thomas Kunkel, Laboratory of Genetics, National Institute of Environmental Health Sciences, Research Triangle Park, N.C., 27709. Vectors pBR327 and M13mp9 can be obtained from Pharmacia (Piscataway, N.J.). Plasmid pUC18, described by Yanisch-Perron et al. (Gene (1985) 33: 103-119), can be obtained from Pharmacia (Piscataway, N.J.). Vector M13mp19 can be obtained from New England Biolabs (Beverly, Mass.).

*E. coli* JM101 F$^-$, which lacks the F factor beta-galactosidase complementary sequences, is created from *E. coli* JM101 to avoid homologous recombination between the plasmid and chromosomal sequences. Conversion of *E. coli* JM101 to JM101 F$^-$ is achieved in accordance with the method described by Hirota, Y., Proc. Nat's 1. Acad. Sci., U.S.A. (1960) 46: 57-64.

The growth media for the bacteria and conditions for transformation and selected of *E. coli* cells carrying expression vehicles containing a conventional antibiotic resistance marker are, for example, as essentially described in Maniatis et al. eds. (1982) *Molecular Cloning A Laboratory Manual*, Cold Spring Harbor Laboratory, Cold Spring Harbor, N.Y.

All bacterial growth media components and antibiotics are obtained from either Sigma (St. Louis, Mo.) or Difco Laboratories (Detroit, Mich.). Specifically, cells containing the desired plasmids are grown in the presence of 50 μg/ml kanamycin to select for the presence of expression vehicles containing a kanamycin resistance (Kn$^r$) marker. Cells carrying expression vehicles containing ampicillin resistance (amp$^r$) or gentamicin resistance (Gm$^r$) markers are grown in medium containing 200 μg/ml ampicillin or 10 μg/ml gentamicin, respectively. For *P. testosteroni* 500 μg/ml gentamicin is used for selection. The growth media used is LB medium (Maniatis et al., 1982) and growth achieved by incubation of bacterial cultures at 30° C. or 37° C. with shaking at 250 rpm.

Rifampicin resistance derivatives of the above bacterial strains, except the *E. coli* strains, are generated to provide a counter-selectable marker for conjugable transfer of the desired vectors. A 100 μl aliquot of each strain grown overnight at 30° C. on LB media is spread on the surface of a petri plate containing LB medium with 50 μg/ml rifampicin. Spontaneous rifampicin resistance mutants are selected and purified by restreaking an isolated colony on another LB plate containing rifampicin (50 μg/ml). These rifampicin-resistant derivatives are useful in triparental matings with HB101(pRK2013) and the appropriate *E. coli* culture containing the desired plasmid using the method described by Ditta, G. S. et al. (Ditta, G. S. et al. Proc. Nat'l. Acad. Sci., U.S.A., 1980, 77: 7347-7351). Selection of recombinant cells capable of producing beta-galactosidase are selected on LB medium containing rifampicin (50 μg/ml) and kanamycin (50 μg/ml), described above.

Induction of transcription from the *E. coli* recA promoter is conducted as follows. Recombinant bacterial carrying expression vehicles are grown in LB medium (Maniatis et al., 1982) containing 50 μg/ml kanamycin to exponential phase, typically to a cell density of about 100 Klett Units (measured with a Klett-Summerson meter, Klett Mfg. Co. New York City, N.Y.). A 5 ml sample is then removed and nalidixic acid (10 mg/ml in 0.1N NaOH) added to the remainder of the culture to a final concentration of 50 μg/ml naladixic acid. Growth is continued for several hours after induction with aliquots taken a designated (e.g. hourly) intervals to determine the peak of desired protein production. A high level of aeration is maintained throughout the bacterial growth in order to achieve maximal production of the desired gene product and the temperature of the culture is maintained at either 30° C. or 37° C.

The levels of desired polypeptide produced in recombinant host cells are determined by such protein-specific assays as enzyme activity and Western immunoblotting (Renart et al. (1979) Proc. Nat'l. Acad. Sci., U.S.A. 76: 3116-3120). For example, the levels of beta-galactosidase (β-gal) produced are determined as follows. Cells containing expression vehicles are grown in LB medium containing an antibiotic concentration appropriate for the resistance marker carried on the expression vehicle as described above, until they reached an optical density of about 100 Klett units. Cells from 5.0 ml of culture are harvested by centrifugation and the pellet is resuspended in 1.0 ml Z Buffer (comprising 60 mM monobasic sodium phosphate, 40 mM dibasic sodium phosphate, 10 mM potassium chloride, 50 mM beta-mercaptoethanol, adjusted to pH 7.0). The extract is diluted 2 to 100 fold with Z Buffer prior to assay in order to get a measureable activity. 25 to 100 μl of diluted sample is added to Z Buffer to a final volume of 1.0 ml. The tubes are equilibrated at 37° C. and 0.2 ml of O-nitrophenyl-β-galactopyranoside (ONPG) (4 mg/ml in 0.1M phosphate buffer, pH 7.0) is added. The reaction is allowed to proceed until a noticeable yellow color developed. The reaction is then stopped by adding 0.5 ml 1M Na$_2$CO$_3$, and the absorbance is measured at 420 nm. Beta-galactosidase activity is expressed as μmoles of product formed per minute per mg of protein using the μM extinction coefficient of 4.5 for the ONPG in accordance with the method described by Miller, J. W. (1972) *Experiments in Molecular Genetics*, Cold Spring Harbor Laboratory, Cold Spring Harbor, N.Y. Protein concentration is determined as described by Braford, M. M., Anal. Biochem. (1976) 72: 248-254.

The levels of porcine growth hormone (PGH) are determined as previously described.

EXPANDED EXAMPLE 1

This example demonstrates the construction of various expression vehicles comprising an *E. coli* recA promoter operatively linked to a synthetic G10L sequence and/or a structural gene (e.g. DNA sequence encoding a desired peptide). Specifically, this example demonstrates the construction of broad host range expression vehicles comprising an *E. coli* recA promoter (prec) operatively linked to the following: an *E. coli* beta-galactosidase (lacZ) structural gene and a consensus *E. coli* ribosome binding (S.D.) sequence; an *E. coli* beta-galactosidase structural gene and a G10L sequence; a porcine growth hormone (PGH) structural gene and a G10L sequence.

a. prec-G10L-LacZ

As shown in FIG. 13, an expression vehicle designated pMON5542 containing an *E. coli* recA promoter (prec) operatively linked to a G10L sequence and LacZ structural gene is created as follows. Plasmid pNM480 described by Nigel P. Minton (Gene (1984) 31: 269-273) which carries the LacZ structural gene is cleaved with NcoI and the NcoI site removed by filling in with *E. coli* DNA polymerase, Klenow fragment, and then religated with T4 DNA ligase to create pMON5526 (FIG. 13). Plasmid pMON5515 is cleaved with AvaI and NcoI and the small AvaI/NcoI fragment carrying prec and G10L, the ends of which are rendered blunt-ended with Klenow polymerase, is isolated and mixed, in the presence of T4 DNA ligase with pMON5526 previously cleaved with SmaI. The ligation mixture is then used to transform *E. coli* JM101 cells and transformants selected by growth in ampicillin-containing medium. The desired resultant vector, designated pMON5527 (FIG. 13), containing a prec, G10L and LacZ structural gene is confirmed by restriction digestion and plating on MacConkey agar plates containing ampicillin.

Plasmid pEMBL18 described by L. Dente eds. et al. in *DNA Cloning* vol. 1. "A Practical Approach" pgs. 101-108, IRL Press, 1985, McLean, Va. is cleaved with PvuII and the small fragment removed. Plasmid pMON5527 is cleaved with DraI and an approximately 4800-5000 base pair (bp) fragment containing the prec, G10L and LacZ sequences isolated and mixed, in the presence of T4 DNA ligase, with the PvuII cleaved pEMBL18 plasmid. The ligation mixture is then used to transform *E. coli* MC1000 and transformants selected by growth on plates comprising MacConkey agar containing ampicillin. The resultant expression vehicle carrying prec operatively joined to a G10L and LacZ structural gene sequences is designated pMON5542 (FIG. 13). The operative joining of said sequences is confirmed by digestion with restriction enzymes.

In order to create a broad host range expression vehicle containing the prec, G10L and LacZ sequences, pMON5542 (FIG. 14) is joined to a broad host range plasmid pMON7051. Plasmid pMON7051, which contains an origin of replication and IncQ replication genes (collectively, "IncQ replicon," denoted "IncQ" in FIG. 15) operable in a wide range of Gram-negative bacteria, is constructed as follows. The gentamicin resistance gene (Gm$^r$) is isolated from plasmid pPH1JI (Hirsch, P. R. and an Beringer, J. E., 1984, Plasmid 12: 139-141) as an EcoRI/BamHI fragment. The Gm$^r$-containing EcoRI/BamHI fragment is then ligated into the *E. coli* cloning plasmid pKC7 (Rogers, S. G. et al., 1979, Gene 7: 79) which had been cleaved with EcoRI and BamHI. The ligation mixture is used to transform *E. coli* and transformants selected by growth in medium containing both ampicillin and gentamicin. The size of the Gm$^r$ gene is then reduced to about 1900 bp by deletion using SphI at the BamHI-proximal end. An EcoRI-proximal Hind III site is then inactivated by treatment of this site with Klenow polymerase and re-ligation. The EcoRI/SphI Gm$^r$-containing fragment is then cloned into an IncQ replicon, RSF1010, described by Geurry, P. et al., 1974, J. Bacteriol. 117: 619-630, to form pMON7051. Specifically, the Gm$^r$ gene fragment is first inserted into the most distal SphI site in RSF1010, thereby inactivating the streptomycin resistance gene in RSF1010. The upstream sulphanilamide resistance gene and its promoter are then removed by deleting an 800 bp PstI fragment from the IncQ replicon. Plasmid pMON5542 is then joined to pMON7051 by first cleaving both plasmids with EcoRI and then mixing the cleaved plasmids in the presence of T4 DNA ligase. The ligation mixture is then used to transform *E. coli* JM101 F$^-$ and transformants selected by growth on medium-containing both ampicillin (200 μg/ml) and gentamicin (10 μg/ml).

The resulting broad host range plasmids containing an *E. coli* recA promoter operatively joined to a G10L sequence and LacZ structural gene in either orientation with respect to the gentamicin resistance gene are designated pMON5757 and pMON5758, respectively, (FIG. 14).

An additional broad host range expression vehicle, designated pMON5014 (FIG. 15), comprising an *E. coli* recA promoter operably joined to a G10L sequence and LacZ structural gene is constructed as follows.

Plasmid pMON5527 (FIG. 13) is digested with EcoRI and DraI and an approximately 4.4 kilobase (kb) fragment containing prec, G10L and LacZ structural gene sequences isolated. This 4.4 kb fragment is then inserted into pMON7030 previously digested with EcoRI and HpaI. Plasmid pMON7030, an about 9.4 kb plasmid, comprises a pNH9279 plasmid (Grinter, N. J., 1983, Gene 21: 133-143), obtainable from the National Collection of Industrial Bacteria, Scotland, under accession number NCIB 11715, digested with PstI to delete the Tn7 sequences while retaining the kanamycin (km$^r$) resistance gene and broad host range replication of origin and replication genes. The resultant broad host range plasmid pMON5014 (FIG. 15) comprises prec operatively joined to a G10L sequence and LacZ structural gene and carries a kanamycin resistance marker to allow selection of host cells transformed with pMON5014.

b. prec-consensur S.D.-LacZ

Creation of a pEMBL vector comprising an E. coli recA promoter (prec) operatively joined to an E. coli consensus ribosome binding site (SD) and DNA sequence encoding beta-galactosidase (LacZ) structural gene, which vector is designated pMON5575, is as follows.

Plasmids pMON6002, obtained from E. coli JM101 having ATCC accession number 67044, and pMON5515, described above, are both individually digested with NcoI and EcoRI and then mixed in the presence of T4 DNA ligase. The ligation mixture is then used to transform E. coli JM101 cells and transformants selected by growth in ampicillin-containing medium. The desired vector, designated pMON5514 carrying a prec operatively joined to a consensus S.D. and an atriopeptigen coding sequence (APgen) is confirmed by digestion with restriction enzymes showing the absence of a G10L sequence and presence of an atrialpeptigen coding sequence. Plasmid pMON5514 is cleaved with AvaI and NcoI to obtain an about 1200 bp fragment containing prec and consensus S.D. sequences. This fragment is then purified and inserted into pMON5526, (FIG. 13), at the SmaI site. The resulting plasmid is designated pMON5540 and comprises a pBR322 derivative plasmid containing a prec operatively joined to a consensus S.D. and lacZ structural gene. The pMON5575 pEMBL-derivative plasmid is created by replacing the EcoRI/HindIII region of pMON5542, which carries the prec and G10L sequences, with the EcoRI/Hind III fragment from pMON5540, which carries the prec and consensus S.D. sequences.

The broad host range expression vehicle, designated pMON5759 (FIG. 15), is constructed by fusing pMON5575 with pMON7051. Specifically, pMON5575 and pMON7051 are individually digested with EcoRI, ligated and then used to transform E. coli JM101 F$^-$, and transformants selected by growth in gentamicin- and ampicillin-containing medium. The resultant broad host range expression vehicle, pMON5759, comprises prec operatively joined to a consensus ribosome binding site (SD) and LacZ structural gene. Vector pMON5759 also contains a Gm$^r$ gene and IncQ replicon.

c. precA-G10L-PGH

A broad host range expression vehicle, designated pMON5756, carrying an E. coli promoter (prec) operatively joined to a G10L and porcine growth hormone (PGH) structural gene is created as follows. Plasmid pMON5647, the construction of which is described above in Example 2h, is cleaved with EcoRI and mixed, in the presence of T4 DNA ligase, with pMON7051, previously cleaved with EcoRI, and the ligation mixture used to transform E. coli JM101 F$^-$. Transformants are selected by growth on ampicillin- and gentamicin-containing media and the formation of the broad host range expression vehicle, pMON5756 (FIG. 15), confirmed by restriction endonuclease digestion.

EXPANDED EXAMPLE 2

This example demonstrates the ability of G10L sequences to provide a functional ribosome binding site in heterologous Gram-negative bacteria and the ability of an E. coli recA promoter (prec) to cause expression of a desired structural gene in heterologous (e.g. non-E. coli) Gram-negative bacteria. In this and the following examples, the G10L sequence employed provides the ribosome binding site required for the translation of mRNA molecules encoding the desired protein.

As shown in Table I, below, various Pseudomonas species transformed with an expression vehicle containing prec operably joined to a G10L sequence and an E. coli beta-galactosidase structural gene (LacZ) exhibited high levels of uninduced beta-galactosidase ($\beta$-gal) activity. E. coli JM101 F$^-$ and Pseudomonas (P). fluorescens 701E1 and P. testosteroni are all individually transformed with a $\beta$-gal expression vehicle, pMON5014, described above, in accordance with the methods previously described. All transformed bacteria are grown at 30° C. in LB medium containing 50 $\mu$g/ml kanamycin as previously described. Basal levels of $\beta$-gal produced in the transformed bacteria are determined as described above, and are expressed in micromoles ($\mu$M) per minute (min) per milligram (mg) of protein. Surprisingly, both recombinant Pseudomonas species assayed showed higher levels of $\beta$-gal production than the transformed E. coli host in which the LacZ structural gene is endogenous.

TABLE I

| Expression of $\beta$-gal Under Non-Inducing Conditions | | |
|---|---|---|
| Organism | Plasmid | $\beta$-gal Specific Activity ($\mu$M/min/mg) |
| E. coli JM101 F$^-$ | pMON5014 | 2.4 |
| P. fluorscens (701 E1) | pMON5014 | 15 |
| P. testosteroni (ATCC 17409) | pMON5014 | 10 |

As shown in Table I, above, G10L sequences, when operably joined to prec and the LacZ structural gene, are able to function as ribosome binding sites in both E. coli and the various transformed Pseudomonas (P.) species. Indeed, both recombinant Pseudomonas species tested exhibited higher levels of $\beta$-gal production than the E. coli species transformed with the prec- and G10L-containing expression vehicle.

As shown in Tables 2-4, below, expression vehicles comprising a G10L sequence operably joined to an prec and beta-galactosidase structural gene (LacZ) are capable of causing expression of beta-galactosidase ($\beta$-gal) in such heterologous Gram-negative bacteria as Pseudomonas, Serratia and Erwinia under conditions which specifically induce (e.g. regulate) prec controlled expression.

In one study, E. coli JM101, P. fluorescens 701E1 and P. testosteroni are transformed with expression vehicle pMON5014 (FIG. 15). The transformed (recombinant) bacteria are grown in LB medium at 30° C., unless otherwise specified, and induced with nalidixic acid (final concentration of 50 μg/ml) as previously described. β-gal activity is then measured at 4 hours post-induction and the level of induction determined by comparing the four hour level of β-gal activity with the β-gal activity level just prior to addition of nalidixic acid (0 hours). the results of this study are shown in Table 2, below, and clearly demonstrate that the G10L sequence provides a functional ribosome binding site under conditions in which gene expression is regulated (i.e. induced) in such other non-E. coli (e.g. heterologous) Gram-negative genera as Pseudomonas.

TABLE 2

Induction of β-gal Activity by Nalidixic Acid

| Organism* | Induction Time (hr) | Sp Act μM/min/mg |
|---|---|---|
| E. coli JM101 (30° C.) | 0 | 3.5 |
|  | 4 | 9.9 |
| E. coli JM101 (37° C.) | 0 | 3.5 |
|  | 4 | 11.0 |
| P. fluorescens (701E1) | 0 | 16.0 |
|  | 4 | 51.0 |
| P. testosteroni (ATCC 17409) | 0 | 9.7 |
|  | 4 | 14.0 |

*All organisms contained plasmid pMON5014 (FIG. 15).

The efficient induction (e.g. regulation) of prec which controls β-gal expression is confirmed by sodium dodecylsulfate-polyacrylamide gel electrophoresis (SDS-PAGE). Specifically, about 5 Klett Units of culture is separated on 9% (w/v) SDS-PAGE gels and the gels stained with silver as described by Wray, W. et al., 1981, Anal. Biochem. 118: 197-203.

Another demonstration of the efficient functioning of G10L sequences in a broad range of Gram-negative bacteria other than E. coli is shown in Table 3, below. Specifically, three additional species of Pseudomonas and two additional genera of Gram-negative bacteria, Erwinia (E.) and Serratia (S.), are transformed with an expression vehicle comprising a G10L sequence operatively joined to prec and a LacZ structural gene. The expression vector employed is pMON5757, described above and shown in FIG. 15. The levels of β-gal activity in bacteria transformed with a control vector, pMON5761, which is identical to pMON5757 except that the prec sequences have been deleted, is also included to show that the β-gal activity detected is indeed caused by prec.

Expression plasmids pMON5757 (FIG. 15) and pMON5761 (FIG. 15) are introduced by transformation or conjugation into the organisms listed in Table 3, below, as previously described. Spontaneous rifampicin resistant derivatives of each organism are selected and the plasmids mated into the appropriate organism by selected for gentamicin and rifampicin resistance. All recombinant organisms containing the appropriate plasmids are then grown and induced with nalidixic acid as previously described except that gentamicin as used instead of kanamycin.

TABLE 3

Induction of β-gal Activity in Heterologous Bacteria by Nalidixic Acid

| Organism | Plasmid* | Induction (hr) | β-galactosidase μM/min/mg |
|---|---|---|---|
| E. coli (30° C.) | pMON5757 | 3 | 33.00 |
|  | pMON5761 | 3 | 0.016 |
| E. coli (37° C.) | pMON5757 | 3 | 77.00 |
|  | pMON5761 | 3 | 0.27 |
| S. marcescens | pMON5757 | 3 | 3.60 |

TABLE 3-continued

Induction of β-gal Activity in Heterologous Bacteria by Nalidixic Acid

| Organism | Plasmid* | Induction (hr) | β-galactosidase μM/min/mg |
|---|---|---|---|
|  | pMON5761 | 3 | 0.08 |
| E. herbicola | pMON5757 | 3 | 67.00 |
|  | pMON5761 | 3 | 0.53 |
| P. putida | pMON5757 | 3 | 23.00 |
|  | pMON5761 | 3 | 0.40 |
| P. aeruginosa | pMON5757 | 3 | 13.00 |
|  | pMON5761 | 3 | 0.87 |
| P. syringae | pMON5757 | 3 | 22.00 |
|  | pMON5761 | 3 | 0.19 |

*pMON5757 contains the recA promoter driving β-gal expression, whereas pMON5761 is the identical construct without the recA promoter.

The results shown in Table 3, above, clearly demonstrate the functionality of the G10L sequence in a wide range of Gram-negative organisms. As predicted, only a low level of LacZ gene expression is seen for cultures in which prec is deleted.

The results of experiments demonstrating regulatable expression of a structural gene encoding porcine growth hormone (PGH) in various Gram-negative bacteria when the gene is operably joined to prec and a G10L sequence are shown in Table 4, below. The previously described expression vector pMON5756 (FIG. 15), which comprises prec operably joined to a G10L sequence and PGH structural gene, is inserted into the organisms listed in Table 4, below, and the resultant recombinant organisms grown at 30° C. in ampicillin-containing LB medium. The cultures are induced with 50 μg/ml nalidixic acid, as previously described and assayed at times 0 hours and 3 hours post-induction for PGH production by Western immunoblotting of a 15% (w/v) SDS-PAGE gel and thereafter scanned for total protein with a LKB Ultroscan XL laser densitometer (LKB, Uppsala, Sweden).

TABLE 4

Porcine Growth Hormone Accumulation

| Organism* | Time (hr) Post-Induction | Level of Accumulation** |
|---|---|---|
| E. coli JM101F⁻ | 3 | + + + + + |
| P. testosteroni | 3 | + + + + |
| P. fluorescens | 3 | + + + |
| P. putida | 3 | + + |
| S. marcescens | 3 | + + + |

*All organisms are transformed with expression vehicle pMON5756
**Levels of PGH production are ascertained by Western immunoblotting and scanning with a LKB Ultroscan XL laser densitometer As can be seen by the results presented in Table 4, above, three different species of Pseudomonas and an additional genus of Gram-negative bacteria all show inducible expression of PGH and, thus, the respective functioning of both prec and the G10L sequence.

EXPANDED EXAMPLE 3

This example demonstrates that desired protein production in Gram-negative bacteria can be enhanced by the operative joining of a G10L sequence to prec and a desired structural gene.

E. coli JM101F⁻ is transformed with the expression vectors indicated in Table 5B, below, and transformants selected as described above, except that 10 μg/ml of gentamicin is used for selection. The desired expression vectors (see Tables 5A and 5B) are conjugated into the Pseudomonas species listed in Tables 5A and 5B, below, using 50 μg/ml gentamicin and rifampicin for *P. fluorescens* strain 701E1 and *P. fluorescens* strain 1141F1, and 250 μg/ml gentamicin and rifampicin for *P. testosteroni*. All transformed organisms are grown and induced with nalidixic acid as previously described. Plasmids pMON5760 and pMON5761 are constructed by deleting a specific number of nucleotides so as to specifically remove prec.

TABLE 5A
Enhancement of β-gal Accumulation by G10L Sequences

| Plasmid | Time (hr) Post-Induction | *P. flourescens* 701E1 β-gal* | Enh.** | *P. flourescens* 1141F1 β-gal* | Enh.** |
|---|---|---|---|---|---|
| pMON5757† (prec G10L) | 4 | 76.0 | 14.3 | 33.0 | 20.6 |
| pMON5758† (prec G10L) | 4 | 87.0 | 16.4 | 37.0 | 23.1 |
| pMON5759† (prec cons) | 4 | 5.3 | — | 1.6 | — |
| pMON5760† ( G10L) | 4 | 1.6 | — | 1.5 | — |
| pMON5761† ( G10L) | 4 | 0.64 | — | 0.40 | — |

† denotes plasmids which have the LacZ gene in the same orientation.
*β-gal specific activity expressed in μM/min/mg protein.
**denotes fold enhancement in β-gal protein activity for plasmids containing a G10L sequence (G10L) as compared to a consensus S.D. (cons) sequence.

TABLE 5B
Enhancement of β-gal Accumulation by G10L Sequences

| Plasmid | Time (hr) Post-Induction | *P. testosteroni* 701E1 β-gal* | Enh.** | *E. coli JM101F⁻* β-gal* | Enh.** |
|---|---|---|---|---|---|
| pMON5757† (prec G10L) | 4 | 18.0 | 19.0 | 42.0 | 25.0 |
| pMON5758† (prec G10L) | 4 | 20.0 | 21.1 | 40.0 | 23.5 |
| pMON5759† (prec cons) | 4 | 0.95 | — | 1.9 | — |
| pMON5760† ( G10L) | 4 | 0.46 | — | 0.41 | — |
| pMON5761† ( G10L) | 4 | 1.1 | — | 0.037 | — |

† denotes plasmids which have the LacZ gene in the same orientation.
*β-gal specific activity expressed in μM/min/mg protein.
**denotes fold enhancement in β-gal protein activity for plasmids containing a G10L sequence (G10L) as compared to a consensus S.D. (cons) sequence.

Induction of β-gal production observed via enzyme analysis in Tables 5A and 5B, above, is confirmed for both *E. coli* and *P. fluorescens* 701E1 by protein analysis on 9% (w/v) SDS-PAGE in accordance with methods previously described.

As shown in Tables 5A and 5B, above, all transformed organisms show a 14 to 25 fold higher level of β-gal production with the vectors pMON5757 and pMON5758 which contain a G10L sequence compared to the *E. coli* consensus (cons) ribosome binding site. The low levels of β-gal accumulation observed when prec is deleted is believed to be due to read-through transcription from other promoters present on the expression vectors. The foregoing results clearly demonstrate the ability of the G10L sequences of the present invention to enhance desired protein production in a wide range of microorganisms.

The foregoing examples illustrate preferred embodiments of the present invention and are not intended to limit the invention's scope in any way. While this invention has been described in relation to its preferred embodiments, various modifications thereof will be apparent to one skilled in the art from reading this application.

REFERENCES

1. Alton, N. K. and Vapnek, D. (1979) *Nature* 282: 864–869.
2. Berget, P. B. et al., (1983) *J. Mol. Biol.* 164:561–572.
3. Brosius, J., Palmer, M. L. Kennedy, J. P. and Noller, H. F. (1978) *Proc. Nat'l. Acad. Sci., U.S.A.* 75: 4801–4805.
4. DeBoer et al. (1982) in *Promoters: Structure and Function,* Chamberlin, M. J. and Rodriguez, R. eds., chapter 293.
5. Dunn, J. J. and Studier, W. F. (1983) *J. Mol. Biol.* 166: 477–535.
6. Goeddel et al. (1979) *Nature* 281: 544–548.1
7. Gold et al (1984) *Proc. Nat'l. Acad. Sci., U.S.A.* 81: 7061–7065.
8. Goldberg, S. D., Flick, J. S. and Rogers, S. G. (1984) *Nucleic Acids Res.* 12: 4665–4677.
9. Gren, E. J. (1984) *Biochimie* 66: 1–29.
10. Gutell, R. R., Wieser, B., Woese, C. R. and Noller, H. F. (1985) *Progr. Nucleic Acids Res. & Mol. Biol.* 32: 155–216.
11. Holmes, M. W., Platt, T. and Rosenberg, M. (1983) *Cell* 32:1029–1032.
12. Habig, W. H. And Jakoby, W. B., (1981) *Methods in Enzymol.* 77:398.
13. Kalnins, A., Otto, K., Ruether, U. and Mueller-Hill, B. (1983) *EMBO J* 2: 593–597.
14. Kunkel (1985) *Proc. Nat'l. Acad. Sci., U.S.A.* 82:488–492.
15. Laemmli, U. K. (1970) *Nature* 227: 680–685.
16. Maniatis, Fritsch and Sambrook, eds. (1982) *Molecular Cloning: A Laboratory Manual,* Cold Spring Harbor Laboratory, Cold Spring Harbor, N.Y.
17. Messing et al (1982) *Gene* 19:629.
18. Minton, N. P. (1984) *Gene* 31: 269–273.
19. Miozzari and Yanofsky (1978) *J. Bacteriol.* 133: 1457–1466.
20. Norris et al. (1983) *Nuc. Acid. Res.* 11: 5103–5112.
21. O'Farrell, P. Z., Goodman, H. M. and O'Farrell, P. H. (1977) *Cell* 12: 1133–1142.
22. Olins, P. O. et al. (1981) *Cell* 26:205–214.
23. Parker, M. L., Christensen, A. C., Boosman, A., Stockard, J., Young E. T. and Doermann, A. H. (1984) *J. Mol. Biol.* 180: 399–146.
24. Renart, J., Reiser, J. and Stark, G. R. (1979) *Proc. Nat'l. Acad. Sci., U.S.A.* 76:3116–3120.
25. Rosenburg and Court (1979) *Ann. Review of Genet.* 13: 319–353.
26. Sanger et al. (1977) *Proc. Nat'l. Acad. Sci., U.S.A.* 74: 5463.
27. Scherer, G. F. E., Walknishaw, M. D., Arnott. S. and Morre, D. J. (1980) *Nucl. Acids Res.* 8: 3895–3905.
28. Seeburg et al. (1983) *DNA* 21: 37–45.
29. Shine, J. and Dalgarno (1974) *Proc. Nat'l. Acad. Sci., U.S.A.* 71: 1342–1346.
30. Soberon, X., Covarrubias, X. and Bolivar, F. (1980) *Gene* 9: 287–305.
31. Vaitukaitis, J. L. (1981). *Methods in Enzymology* 73: 46–52.
32. Von Hippel, P. et al., (1984) *Ann. Rev. Biochem.* 53:389–446.
33. Woese, C. R., Gutell, R. R., Gupta, R. and Noller, H. F. (1983) *Microbiol. Rev.* 47: 621.
34. Yanisch-Perron, C., Viera, J. and Messing, J. (1985) *Gene* 33:103–119.
35. Zoller and Smith (1982) *Nuc. Acids Res.* 10: 6487–6500.

36. Zoller and Smith (1983) *Methods in Enzymol.* 100: 468-500.

What is claimed:

1. In a method for producing protein in bacteria by expressing a recombinant gene coding for a heterologous protein, the improvement which comprises expressing a recombinant gene containing a promoter operably linked to a non-translated DNA sequence which consists of about the first 100 nucleotides immediately 5' to the translation start codon of the bacteriophage T7 gene 10 coding sequence which is upstream of a DNA sequence coding for a heterologous protein, and producing heterologous protein.

2. In a method for producing protein in bacteria by expressing a recombinant gene coding for a heterologous protein, the improvement which comprises expressing a recombinant gene containing a promoter operably linked to the nucleotide sequence of FIG. 1 which is upstream of a DNA sequence coding for a heterologous protein, and producing heterologous protein.

3. In a method for producing protein in bacteria by expressing a recombinant gene coding for a heterologous protein, the improvement which comprises expressing a recombinant gene containing a promoter operably linked to the nucleotide sequence of FIG. 2 which is upstream of a DNA sequence coding for a heterologous protein, and producing heterologous protein.

4. The method of claim 1 in which the heterologous protein is selected from the group consisting of bovine growth hormone and porcine growth hormone.

5. The method of claim 1 in which the bacteria is selected from a group consisting of Escherichia, Serratia, Pseudomonas and Erwinia.

6. The method of claim 5 wherein the bacteria is selected from a group consisting of *Pseudomonas fluorescens, Pseudomonas putida, Pseudomonas testosteroni, Pseudomonas aerugginosa, Pseudomonas syringea, Serratia marcescens* and *Erwinia herbicola*.

7. In a method for producing proteins in bacteria by expressing a recombinant gene coding for a heterologous protein, the improvement which comprises operably linking to said recombinant gene coding for said heterologous protein a translational enhancer DNA about 7-9 nucleotides in length which encodes, a mRNA sequence that is capable of forming a stable complementary base-paired interaction with a rRNA sequence, in which the said rRNA sequence is a domain equivalent to that for *E. coli* shown in FIG. 3.

8. The method as recited in claim 7 wherein said complementary base-paired mRNA sequence is about 7-9 nucleotides.

* * * * *